US012667417B2

(12) United States Patent
Rodriguez Soto et al.

(10) Patent No.: US 12,667,417 B2
(45) Date of Patent: Jun. 30, 2026

---

(54) SYSTEMS AND METHODS FOR CYLINDRICAL CAGE MAPPING AND ABLATION CATHETERS HAVING INTEGRATED ELECTRODES

(71) Applicant: Biosense Webster (Israel) Ltd., Yokneam (IL)

(72) Inventors: Juan Rodriguez Soto, Irvine, CA (US); Mohammad Abbas, Orange, CA (US); Babak Ebrahimi, Lake Forest, CA (US); Pieter Emmelius Van Niekerk, Rancho Santa Margarita, CA (US); Shubhayu Basu, Anaheim, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 268 days.

(21) Appl. No.: 18/509,900

(22) Filed: Nov. 15, 2023

(65) Prior Publication Data

US 2024/0216053 A1 Jul. 4, 2024

Related U.S. Application Data

(60) Provisional application No. 63/477,773, filed on Dec. 29, 2022.

(51) Int. Cl.
*A61B 18/14* (2006.01)
*A61B 18/00* (2006.01)
(Continued)

(52) U.S. Cl.
CPC .......... *A61B 18/1492* (2013.01); *A61B 18/16* (2013.01); *A61B 2018/0016* (2013.01);
(Continued)

(58) Field of Classification Search
CPC ................ A61B 18/1492; A61B 18/16; A61B 2090/0811; A61B 2018/0016;
(Continued)

(56) References Cited

U.S. PATENT DOCUMENTS 4,699,147 A    10/1987   Chilson et al.
4,940,064 A     7/1990   Desai
(Continued)

FOREIGN PATENT DOCUMENTS

CN    111248993 A    6/2020
CN    111248996 A    6/2020
(Continued)

OTHER PUBLICATIONS

Extended European Search Report and Opinion dated May 14, 2024, from corresponding European Application No. 23219649.3.

*Primary Examiner* — Linda C Dvorak
*Assistant Examiner* — Abigail Bock

(57) ABSTRACT

The disclosed technology includes basket catheters comprising a generally cylindrical structure having electrodes attached thereto. The disclosed technology can include a structural unit for an end effector comprising a proximal member extending along a longitudinal axis. The proximal member can define a plurality of divergent curvilinear members. Each divergent curvilinear member can define two meander members extending along the longitudinal axis such that the structural unit comprises a plurality of meander members. Each of the plurality of meander members can be connected to a respective convergent curvilinear member of a plurality of convergent curvilinear members. The structural unit can further comprise a distal member connected to the plurality of convergent curvilinear members.

20 Claims, 8 Drawing Sheets

(51) Int. Cl.
*A61B 18/16* (2006.01)
*A61B 90/00* (2016.01)

(52) U.S. Cl.
CPC ............... *A61B 2018/00267* (2013.01); *A61B 2018/1465* (2013.01); *A61B 2018/1467* (2013.01); *A61B 2018/1475* (2013.01); *A61B 2018/162* (2013.01); *A61B 2090/0811* (2016.02)

(58) Field of Classification Search
CPC .. A61B 2018/00267; A61B 2018/1465; A61B 2018/1475; A61B 2018/162
See application file for complete search history.

(56) References Cited

U.S. PATENT DOCUMENTS

| | | | |
|---|---|---|---|
| 5,215,103 A | 6/1993 | Desai | |
| 5,255,679 A | 10/1993 | Imran | |
| 5,293,869 A | 3/1994 | Edwards et al. | |
| 5,309,910 A | 5/1994 | Edwards et al. | |
| 5,313,943 A | 5/1994 | Houser et al. | |
| 5,324,284 A | 6/1994 | Imran | |
| 5,345,936 A | 9/1994 | Pomeranz et al. | |
| 5,365,926 A | 11/1994 | Desai | |
| 5,391,199 A | 2/1995 | Ben-Haim | |
| 5,396,887 A | 3/1995 | Imran | |
| 5,400,783 A | 3/1995 | Pomeranz et al. | |
| 5,411,025 A | 5/1995 | Webster, Jr. | |
| 5,415,166 A | 5/1995 | Imran | |
| 5,443,489 A | 8/1995 | Ben-Haim | |
| 5,456,254 A | 10/1995 | Pietroski et al. | |
| 5,465,717 A | 11/1995 | Imran et al. | |
| 5,476,495 A | 12/1995 | Kordis et al. | |
| 5,499,981 A | 3/1996 | Kordis | |
| 5,526,810 A | 6/1996 | Wang | |
| 5,546,940 A | 8/1996 | Panescu et al. | |
| 5,549,108 A | 8/1996 | Edwards et al. | |
| 5,558,073 A | 9/1996 | Pomeranz et al. | |
| 5,558,091 A | 9/1996 | Acker et al. | |
| 5,577,509 A | 11/1996 | Panescu et al. | |
| 5,595,183 A | 1/1997 | Swanson et al. | |
| 5,598,848 A | 2/1997 | Swanson et al. | |
| 5,609,157 A | 3/1997 | Panescu et al. | |
| 5,628,313 A | 5/1997 | Webster, Jr. | |
| 5,681,280 A | 10/1997 | Rusk et al. | |
| 5,722,401 A | 3/1998 | Pietroski et al. | |
| 5,722,403 A | 3/1998 | McGee et al. | |
| 5,725,525 A | 3/1998 | Kordis | |
| 5,730,128 A | 3/1998 | Pomeranz et al. | |
| 5,772,590 A | 6/1998 | Webster, Jr. | |
| 5,782,899 A | 7/1998 | Imran | |
| 5,823,189 A | 10/1998 | Kordis | |
| 5,881,727 A | 3/1999 | Edwards | |
| 5,893,847 A | 4/1999 | Kordis | |
| 5,904,680 A | 5/1999 | Kordis et al. | |
| 5,911,739 A | 6/1999 | Kordis et al. | |
| 5,928,228 A | 7/1999 | Kordis et al. | |
| 5,968,040 A | 10/1999 | Swanson et al. | |
| 6,014,579 A * | 1/2000 | Pomeranz ............ A61B 5/6858 | |
| | | | 606/41 |
| 6,014,590 A | 1/2000 | Whayne et al. | |
| 6,119,030 A | 9/2000 | Morency | |
| 6,172,499 B1 | 1/2001 | Ashe | |
| 6,216,043 B1 | 4/2001 | Swanson et al. | |
| 6,216,044 B1 | 4/2001 | Kordis | |
| 6,239,724 B1 | 5/2001 | Doron et al. | |
| 6,332,089 B1 | 12/2001 | Acker et al. | |
| 6,428,537 B1 | 8/2002 | Swanson et al. | |
| 6,456,864 B1 | 9/2002 | Swanson et al. | |
| 6,484,118 B1 | 11/2002 | Govari | |
| 6,574,492 B1 | 6/2003 | Ben-Haim et al. | |
| 6,584,345 B2 | 6/2003 | Govari | |
| 6,600,948 B2 | 7/2003 | Ben-Haim et al. | |
| 6,618,612 B1 | 9/2003 | Acker et al. | |
| 6,690,963 B2 | 2/2004 | Ben-Haim et al. | |
| 6,738,655 B1 | 5/2004 | Sen et al. | |
| 6,741,878 B2 | 5/2004 | Fuimaono et al. | |
| 6,748,255 B2 | 6/2004 | Fuimaono et al. | |
| 6,780,183 B2 | 8/2004 | Jimenez, Jr. et al. | |
| 6,788,967 B2 | 9/2004 | Ben-Haim et al. | |
| 6,837,886 B2 | 1/2005 | Collins et al. | |
| 6,866,662 B2 | 3/2005 | Fuimaono et al. | |
| 6,892,091 B1 | 5/2005 | Ben-Haim et al. | |
| 6,970,730 B2 | 11/2005 | Fuimaono et al. | |
| 6,973,340 B2 | 12/2005 | Fuimaono et al. | |
| 6,980,858 B2 | 12/2005 | Fuimaono et al. | |
| 7,048,734 B1 | 5/2006 | Fleischman et al. | |
| 7,149,563 B2 | 12/2006 | Fuimaono et al. | |
| 7,255,695 B2 | 8/2007 | Falwell et al. | |
| 7,257,434 B2 | 8/2007 | Fuimaono et al. | |
| 7,399,299 B2 | 7/2008 | Daniel et al. | |
| 7,410,486 B2 | 8/2008 | Fuimaono et al. | |
| 7,522,950 B2 | 4/2009 | Fuimaono et al. | |
| 7,536,218 B2 | 5/2009 | Govari et al. | |
| RE41,334 E | 5/2010 | Beatty et al. | |
| 7,756,576 B2 | 7/2010 | Levin | |
| 7,846,157 B2 | 12/2010 | Kozel | |
| 7,848,787 B2 | 12/2010 | Osadchy | |
| 7,869,865 B2 | 1/2011 | Govari et al. | |
| 7,930,018 B2 | 4/2011 | Harlev et al. | |
| 8,007,495 B2 | 8/2011 | McDaniel et al. | |
| 8,048,063 B2 | 11/2011 | Aeby et al. | |
| 8,103,327 B2 | 1/2012 | Harlev et al. | |
| 8,167,845 B2 | 5/2012 | Wang et al. | |
| 8,224,416 B2 | 7/2012 | De La Rama et al. | |
| 8,235,988 B2 | 8/2012 | Davis et al. | |
| 8,346,339 B2 | 1/2013 | Kordis et al. | |
| 8,435,232 B2 | 5/2013 | Aeby et al. | |
| 8,447,377 B2 | 5/2013 | Harlev et al. | |
| 8,456,182 B2 | 6/2013 | Bar-Tal et al. | |
| 8,498,686 B2 | 7/2013 | Grunewald | |
| 8,517,999 B2 | 8/2013 | Pappone et al. | |
| 8,545,490 B2 | 10/2013 | Mihajlovic et al. | |
| 8,560,086 B2 | 10/2013 | Just et al. | |
| 8,567,265 B2 | 10/2013 | Aeby et al. | |
| 8,712,550 B2 | 4/2014 | Grunewald | |
| 8,755,861 B2 | 6/2014 | Harlev et al. | |
| 8,825,130 B2 | 9/2014 | Just et al. | |
| 8,906,011 B2 | 12/2014 | Gelbart et al. | |
| 8,945,120 B2 | 2/2015 | McDaniel et al. | |
| 8,979,839 B2 | 3/2015 | De La Rama et al. | |
| 9,037,264 B2 | 5/2015 | Just et al. | |
| 9,131,980 B2 | 9/2015 | Bloom | |
| 9,204,929 B2 | 12/2015 | Solis | |
| 9,277,960 B2 | 3/2016 | Weinkam et al. | |
| 9,314,208 B1 | 4/2016 | Altmann et al. | |
| 9,339,331 B2 | 5/2016 | Tegg et al. | |
| 9,486,282 B2 | 11/2016 | Solis | |
| 9,554,718 B2 | 1/2017 | Bar-Tal et al. | |
| D782,686 S | 3/2017 | Werneth et al. | |
| 9,585,588 B2 | 3/2017 | Marecki et al. | |
| 9,597,036 B2 | 3/2017 | Aeby et al. | |
| 9,687,297 B2 | 6/2017 | Just et al. | |
| 9,693,733 B2 | 7/2017 | Altmann et al. | |
| 9,782,099 B2 | 10/2017 | Williams et al. | |
| 9,788,895 B2 | 10/2017 | Solis | |
| 9,801,681 B2 | 10/2017 | Laske et al. | |
| 9,814,618 B2 | 11/2017 | Nguyen et al. | |
| 9,833,161 B2 | 12/2017 | Govari | |
| 9,894,756 B2 | 2/2018 | Weinkam et al. | |
| 9,895,073 B2 | 2/2018 | Solis | |
| 9,907,609 B2 | 3/2018 | Cao et al. | |
| 9,974,460 B2 | 5/2018 | Wu et al. | |
| 9,986,949 B2 | 6/2018 | Govari et al. | |
| 9,993,160 B2 | 6/2018 | Salvestro et al. | |
| 10,014,607 B1 | 7/2018 | Govari et al. | |
| 10,028,376 B2 | 7/2018 | Weinkam et al. | |
| 10,034,637 B2 | 7/2018 | Harlev et al. | |
| 10,039,494 B2 | 8/2018 | Altmann et al. | |
| 10,045,707 B2 | 8/2018 | Govari | |
| 10,078,713 B2 | 9/2018 | Auerbach et al. | |
| 10,111,623 B2 | 10/2018 | Jung et al. | |
| 10,130,420 B2 | 11/2018 | Basu et al. | |

(56) References Cited

U.S. PATENT DOCUMENTS

| | | | |
|---|---|---|---|
| 10,136,828 B2 | 11/2018 | Houben et al. | |
| 10,143,394 B2 | 12/2018 | Solis | |
| 10,172,536 B2 | 1/2019 | Maskara et al. | |
| 10,182,762 B2 | 1/2019 | Just et al. | |
| 10,194,818 B2 | 2/2019 | Williams et al. | |
| 10,201,311 B2 | 2/2019 | Chou et al. | |
| 10,219,860 B2 | 3/2019 | Harlev et al. | |
| 10,219,861 B2 | 3/2019 | Just et al. | |
| 10,231,328 B2 | 3/2019 | Weinkam et al. | |
| 10,238,309 B2 | 3/2019 | Bar-Tal et al. | |
| 10,278,590 B2 | 5/2019 | Salvestro et al. | |
| D851,774 S | 6/2019 | Werneth et al. | |
| 10,314,505 B2 | 6/2019 | Williams et al. | |
| 10,314,507 B2 | 6/2019 | Govari et al. | |
| 10,314,648 B2 | 6/2019 | Ge et al. | |
| 10,314,649 B2 * | 6/2019 | Bakos ................ A61B 18/1492 | |
| 10,330,742 B2 | 6/2019 | Govari | |
| 10,349,855 B2 | 7/2019 | Zeidan et al. | |
| 10,350,003 B2 | 7/2019 | Weinkam et al. | |
| 10,362,991 B2 | 7/2019 | Tran et al. | |
| 10,375,827 B2 | 8/2019 | Weinkam et al. | |
| 10,376,170 B2 | 8/2019 | Quinn et al. | |
| 10,376,221 B2 | 8/2019 | Iyun et al. | |
| 10,398,348 B2 | 9/2019 | Osadchy et al. | |
| 10,403,053 B2 | 9/2019 | Katz et al. | |
| 10,441,188 B2 | 10/2019 | Katz et al. | |
| 10,470,682 B2 | 11/2019 | Deno et al. | |
| 10,470,714 B2 | 11/2019 | Altmann et al. | |
| 10,482,198 B2 | 11/2019 | Auerbach et al. | |
| 10,492,857 B2 | 12/2019 | Guggenberger et al. | |
| 10,542,620 B2 | 1/2020 | Weinkam et al. | |
| 10,575,743 B2 | 3/2020 | Basu et al. | |
| 10,575,745 B2 | 3/2020 | Solis | |
| 10,582,871 B2 | 3/2020 | Williams et al. | |
| 10,582,894 B2 | 3/2020 | Ben Zrihem et al. | |
| 10,596,346 B2 | 3/2020 | Aeby et al. | |
| 10,602,947 B2 | 3/2020 | Govari et al. | |
| 10,617,867 B2 | 4/2020 | Viswanathan et al. | |
| 10,660,702 B2 | 5/2020 | Viswanathan et al. | |
| 10,667,753 B2 | 6/2020 | Werneth et al. | |
| 10,674,929 B2 | 6/2020 | Houben et al. | |
| 10,681,805 B2 | 6/2020 | Weinkam et al. | |
| 10,682,181 B2 | 6/2020 | Cohen et al. | |
| 10,687,892 B2 | 6/2020 | Long et al. | |
| 10,702,178 B2 | 7/2020 | Dahlen et al. | |
| 10,716,477 B2 | 7/2020 | Salvestro et al. | |
| 10,758,304 B2 | 9/2020 | Aujla | |
| 10,765,371 B2 | 9/2020 | Hayam et al. | |
| 10,772,566 B2 | 9/2020 | Aujila | |
| 10,799,281 B2 | 10/2020 | Goertzen et al. | |
| 10,842,558 B2 | 11/2020 | Harlev et al. | |
| 10,842,561 B2 | 11/2020 | Mswanathan et al. | |
| 10,863,914 B2 | 12/2020 | Govari et al. | |
| 10,881,376 B2 | 1/2021 | Shemesh et al. | |
| 10,898,139 B2 | 1/2021 | Guta et al. | |
| 10,905,329 B2 | 2/2021 | Bar-Tal et al. | |
| 10,912,484 B2 | 2/2021 | Ziv-Ari et al. | |
| 10,918,306 B2 | 2/2021 | Govari et al. | |
| 10,939,871 B2 | 3/2021 | Altmann et al. | |
| 10,952,795 B2 | 3/2021 | Cohen et al. | |
| 10,973,426 B2 | 4/2021 | Williams et al. | |
| 10,973,461 B2 | 4/2021 | Baram et al. | |
| 10,987,045 B2 | 4/2021 | Basu et al. | |
| 11,006,902 B1 | 5/2021 | Bonyak et al. | |
| 11,040,208 B1 | 6/2021 | Govari et al. | |
| 11,045,628 B2 | 6/2021 | Beeckler et al. | |
| 11,051,877 B2 | 7/2021 | Sliwa et al. | |
| 11,109,788 B2 | 9/2021 | Rottmann et al. | |
| 11,116,435 B2 | 9/2021 | Urman et al. | |
| 11,129,574 B2 | 9/2021 | Cohen et al. | |
| 11,160,482 B2 | 11/2021 | Solis | |
| 11,164,371 B2 | 11/2021 | Yellin et al. | |
| 11,304,642 B2 | 4/2022 | Govari et al. | |
| 2002/0198522 A1 | 12/2002 | Kordis | |
| 2004/0210121 A1 | 10/2004 | Fuimaono et al. | |
| 2006/0009689 A1 | 1/2006 | Fuimaono et al. | |
| 2006/0009690 A1 | 1/2006 | Fuimaono et al. | |
| 2006/0100669 A1 | 5/2006 | Fuimaono et al. | |
| 2007/0093806 A1 | 4/2007 | Desai et al. | |
| 2007/0276212 A1 | 11/2007 | Fuimaono et al. | |
| 2008/0234564 A1 | 9/2008 | Beatty et al. | |
| 2011/0118726 A1 | 5/2011 | De La Rama et al. | |
| 2011/0160574 A1 | 6/2011 | Harlev et al. | |
| 2011/0190625 A1 | 8/2011 | Harlev et al. | |
| 2011/0245756 A1 | 10/2011 | Arora et al. | |
| 2011/0301597 A1 | 12/2011 | McDaniel et al. | |
| 2013/0035686 A1 | 2/2013 | Davis et al. | |
| 2013/0172872 A1 | 7/2013 | Subramaniam et al. | |
| 2013/0172883 A1 | 7/2013 | Lopes et al. | |
| 2013/0178850 A1 | 7/2013 | Lopes et al. | |
| 2013/0190587 A1 | 7/2013 | Lopes et al. | |
| 2013/0296852 A1 | 11/2013 | Madjarov et al. | |
| 2014/0025069 A1 | 1/2014 | Willard et al. | |
| 2014/0052118 A1 | 2/2014 | Laske et al. | |
| 2014/0180147 A1 | 6/2014 | Thakur et al. | |
| 2014/0180151 A1 | 6/2014 | Maskara et al. | |
| 2014/0180152 A1 | 6/2014 | Maskara et al. | |
| 2014/0257069 A1 | 9/2014 | Eliason et al. | |
| 2014/0276712 A1 | 9/2014 | Mallin et al. | |
| 2014/0309512 A1 | 10/2014 | Govari et al. | |
| 2015/0011991 A1 | 1/2015 | Buysman et al. | |
| 2015/0045863 A1 | 2/2015 | Litscher et al. | |
| 2015/0080693 A1 | 3/2015 | Solis | |
| 2015/0105770 A1 | 4/2015 | Amit | |
| 2015/0119878 A1 | 4/2015 | Heisel et al. | |
| 2015/0133919 A1 | 5/2015 | McDaniel et al. | |
| 2015/0208942 A1 | 7/2015 | Bar-Tal et al. | |
| 2015/0250424 A1 | 9/2015 | Govari et al. | |
| 2015/0270634 A1 | 9/2015 | Buesseler et al. | |
| 2015/0342532 A1 | 12/2015 | Basu et al. | |
| 2016/0081746 A1 | 3/2016 | Solis | |
| 2016/0113582 A1 | 4/2016 | Altmann et al. | |
| 2016/0113709 A1 | 4/2016 | Maor | |
| 2016/0183877 A1 | 6/2016 | Williams et al. | |
| 2016/0228023 A1 | 8/2016 | Govari | |
| 2016/0228062 A1 | 8/2016 | Altmann et al. | |
| 2016/0278853 A1 | 9/2016 | Ogle et al. | |
| 2016/0302858 A1 | 10/2016 | Bencini | |
| 2016/0338770 A1 | 11/2016 | Bar-Tal et al. | |
| 2017/0027638 A1 | 2/2017 | Solis | |
| 2017/0065227 A1 | 3/2017 | Marrs et al. | |
| 2017/0071543 A1 | 3/2017 | Basu et al. | |
| 2017/0071544 A1 | 3/2017 | Basu et al. | |
| 2017/0071665 A1 | 3/2017 | Solis | |
| 2017/0095173 A1 | 4/2017 | Bar-Tal et al. | |
| 2017/0100187 A1 | 4/2017 | Basu et al. | |
| 2017/0143227 A1 | 5/2017 | Marecki et al. | |
| 2017/0156790 A1 | 6/2017 | Aujla | |
| 2017/0172442 A1 | 6/2017 | Govari | |
| 2017/0185702 A1 | 6/2017 | Auerbach et al. | |
| 2017/0202515 A1 | 7/2017 | Zrihem et al. | |
| 2017/0221262 A1 | 8/2017 | Laughner et al. | |
| 2017/0224958 A1 | 8/2017 | Cummings et al. | |
| 2017/0265812 A1 | 9/2017 | Williams et al. | |
| 2017/0281031 A1 | 10/2017 | Houben et al. | |
| 2017/0281268 A1 | 10/2017 | Tran et al. | |
| 2017/0296125 A1 | 10/2017 | Altmann et al. | |
| 2017/0296251 A1 | 10/2017 | Wu et al. | |
| 2017/0347959 A1 | 12/2017 | Guta et al. | |
| 2017/0354338 A1 | 12/2017 | Levin et al. | |
| 2017/0354339 A1 | 12/2017 | Zeidan et al. | |
| 2017/0354364 A1 | 12/2017 | Bar-Tal et al. | |
| 2018/0008203 A1 | 1/2018 | Iyun et al. | |
| 2018/0028084 A1 | 2/2018 | Williams et al. | |
| 2018/0049803 A1 | 2/2018 | Solis | |
| 2018/0085064 A1 | 3/2018 | Auerbach et al. | |
| 2018/0132749 A1 | 5/2018 | Govari et al. | |
| 2018/0137687 A1 | 5/2018 | Katz et al. | |
| 2018/0160936 A1 | 6/2018 | Govari et al. | |
| 2018/0160978 A1 | 6/2018 | Cohen et al. | |
| 2018/0168511 A1 | 6/2018 | Hall et al. | |
| 2018/0184982 A1 | 7/2018 | Basu et al. | |
| 2018/0192958 A1 | 7/2018 | Wu | |
| 2018/0206792 A1 | 7/2018 | Auerbach et al. | |

(56)            References Cited

U.S. PATENT DOCUMENTS

| | | | |
|---|---|---|---|
| 2018/0235692 A1 | 8/2018 | Efimov et al. | |
| 2018/0249959 A1 | 9/2018 | Osypka | |
| 2018/0256109 A1 | 9/2018 | Wu et al. | |
| 2018/0279954 A1 | 10/2018 | Hayam et al. | |
| 2018/0303414 A1 | 10/2018 | Toth et al. | |
| 2018/0310987 A1 | 11/2018 | Altmann et al. | |
| 2018/0311497 A1 | 11/2018 | Viswanathan et al. | |
| 2018/0338722 A1 | 11/2018 | Altmann et al. | |
| 2018/0344188 A1 | 12/2018 | Govari | |
| 2018/0344202 A1 | 12/2018 | Bar-Tal et al. | |
| 2018/0344251 A1 | 12/2018 | Harlev et al. | |
| 2018/0344393 A1 | 12/2018 | Gruba et al. | |
| 2018/0360534 A1 | 12/2018 | Teplitsky et al. | |
| 2018/0365355 A1 | 12/2018 | Auerbach et al. | |
| 2019/0000540 A1 | 1/2019 | Cohen et al. | |
| 2019/0008582 A1 | 1/2019 | Govari et al. | |
| 2019/0015007 A1 | 1/2019 | Rottmann et al. | |
| 2019/0030328 A1 | 1/2019 | Stewart et al. | |
| 2019/0053708 A1 | 2/2019 | Gliner | |
| 2019/0059766 A1 | 2/2019 | Houben et al. | |
| 2019/0069950 A1 | 3/2019 | Mswanathan et al. | |
| 2019/0069954 A1 | 3/2019 | Cohen et al. | |
| 2019/0117111 A1 | 4/2019 | Osadchy et al. | |
| 2019/0117303 A1 | 4/2019 | Claude et al. | |
| 2019/0117315 A1 | 4/2019 | Keyes et al. | |
| 2019/0125439 A1 | 5/2019 | Rohl et al. | |
| 2019/0133552 A1 | 5/2019 | Shemesh et al. | |
| 2019/0142293 A1 | 5/2019 | Solis | |
| 2019/0164633 A1 | 5/2019 | Ingel et al. | |
| 2019/0167137 A1 | 6/2019 | Bar-Tal et al. | |
| 2019/0167140 A1 | 6/2019 | Williams et al. | |
| 2019/0188909 A1 | 6/2019 | Yellin et al. | |
| 2019/0201664 A1 | 7/2019 | Govari | |
| 2019/0209089 A1 | 7/2019 | Baram et al. | |
| 2019/0216346 A1 | 7/2019 | Ghodrati et al. | |
| 2019/0216347 A1 | 7/2019 | Ghodrati et al. | |
| 2019/0231421 A1 | 8/2019 | Viswanathan et al. | |
| 2019/0231423 A1 | 8/2019 | Weinkam et al. | |
| 2019/0239811 A1 | 8/2019 | Just et al. | |
| 2019/0246935 A1 | 8/2019 | Govari et al. | |
| 2019/0298442 A1 | 10/2019 | Ogata et al. | |
| 2019/0314083 A1 | 10/2019 | Herrera et al. | |
| 2019/0328260 A1 | 10/2019 | Zeidan et al. | |
| 2019/0343580 A1 | 11/2019 | Nguyen et al. | |
| 2020/0000518 A1 | 1/2020 | Kiernan et al. | |
| 2020/0008705 A1 | 1/2020 | Ziv-Ari et al. | |
| 2020/0008869 A1 | 1/2020 | Byrd | |
| 2020/0009378 A1 | 1/2020 | Stewart et al. | |
| 2020/0015890 A1 | 1/2020 | To et al. | |
| 2020/0022653 A1 | 1/2020 | Moisa | |
| 2020/0029845 A1 | 1/2020 | Baram et al. | |
| 2020/0046421 A1 | 2/2020 | Govari | |
| 2020/0046423 A1 | 2/2020 | Viswanathan et al. | |
| 2020/0060569 A1* | 2/2020 | Tegg | A61B 5/287 |
| 2020/0077959 A1 | 3/2020 | Altmann et al. | |
| 2020/0093539 A1 | 3/2020 | Long et al. | |
| 2020/0129089 A1 | 4/2020 | Gliner et al. | |
| 2020/0129125 A1 | 4/2020 | Govari et al. | |
| 2020/0129128 A1 | 4/2020 | Gliner et al. | |
| 2020/0155224 A1 | 5/2020 | Bar-Tal | |
| 2020/0179650 A1 | 6/2020 | Beeckler et al. | |
| 2020/0196896 A1 | 6/2020 | Solis | |
| 2020/0205689 A1* | 7/2020 | Squires | A61B 5/341 |
| 2020/0205690 A1 | 7/2020 | Williams et al. | |
| 2020/0205737 A1 | 7/2020 | Beeckler | |
| 2020/0205876 A1 | 7/2020 | Govari | |
| 2020/0205892 A1 | 7/2020 | Viswanathan et al. | |
| 2020/0206461 A1 | 7/2020 | Govari et al. | |
| 2020/0206498 A1 | 7/2020 | Arora et al. | |
| 2020/0289197 A1 | 9/2020 | Viswanathan et al. | |
| 2020/0297234 A1 | 9/2020 | Houben et al. | |
| 2020/0297281 A1 | 9/2020 | Basu et al. | |
| 2020/0305726 A1 | 10/2020 | Salvestro et al. | |
| 2020/0305946 A1 | 10/2020 | Desimone et al. | |
| 2020/0397328 A1 | 12/2020 | Altmann et al. | |
| 2020/0398048 A1 | 12/2020 | Krimsky et al. | |
| 2021/0015549 A1 | 1/2021 | Haghighi-Mood et al. | |
| 2021/0022684 A1 | 1/2021 | Govari et al. | |
| 2021/0045805 A1 | 2/2021 | Govari et al. | |
| 2021/0059549 A1 | 3/2021 | Urman et al. | |
| 2021/0059550 A1 | 3/2021 | Urman et al. | |
| 2021/0059608 A1 | 3/2021 | Beeckler et al. | |
| 2021/0059743 A1 | 3/2021 | Govari | |
| 2021/0059747 A1 | 3/2021 | Krans et al. | |
| 2021/0077184 A1 | 3/2021 | Basu et al. | |
| 2021/0082157 A1 | 3/2021 | Rosenberg et al. | |
| 2021/0085200 A1 | 3/2021 | Auerbach et al. | |
| 2021/0085204 A1 | 3/2021 | Auerbach et al. | |
| 2021/0085215 A1 | 3/2021 | Auerbach et al. | |
| 2021/0085387 A1 | 3/2021 | Amit et al. | |
| 2021/0093292 A1 | 4/2021 | Baram et al. | |
| 2021/0093294 A1 | 4/2021 | Shemesh et al. | |
| 2021/0093374 A1 | 4/2021 | Govari et al. | |
| 2021/0093377 A1 | 4/2021 | Herrera et al. | |
| 2021/0100612 A1 | 4/2021 | Baron et al. | |
| 2021/0113822 A1 | 4/2021 | Beeckler et al. | |
| 2021/0121231 A1 | 4/2021 | Basu et al. | |
| 2021/0127999 A1 | 5/2021 | Govari et al. | |
| 2021/0128010 A1 | 5/2021 | Govari et al. | |
| 2021/0133516 A1 | 5/2021 | Govari et al. | |
| 2021/0145282 A1 | 5/2021 | Bar-Tal et al. | |
| 2021/0161592 A1 | 6/2021 | Altmann et al. | |
| 2021/0162210 A1 | 6/2021 | Altmann et al. | |
| 2021/0169421 A1 | 6/2021 | Govari | |
| 2021/0169550 A1 | 6/2021 | Govari et al. | |
| 2021/0169567 A1 | 6/2021 | Govari et al. | |
| 2021/0169568 A1 | 6/2021 | Govari et al. | |
| 2021/0177294 A1 | 6/2021 | Gliner et al. | |
| 2021/0177356 A1 | 6/2021 | Gliner et al. | |
| 2021/0177503 A1 | 6/2021 | Altmann et al. | |
| 2021/0178166 A1 | 6/2021 | Govari et al. | |
| 2021/0186363 A1 | 6/2021 | Gliner et al. | |
| 2021/0186604 A1 | 6/2021 | Altmann et al. | |
| 2021/0187241 A1 | 6/2021 | Govari et al. | |
| 2021/0196372 A1 | 7/2021 | Altmann et al. | |
| 2021/0196394 A1 | 7/2021 | Govari et al. | |
| 2021/0212591 A1 | 7/2021 | Govari et al. | |
| 2021/0219904 A1 | 7/2021 | Yarnitsky et al. | |
| 2021/0278936 A1 | 9/2021 | Katz et al. | |
| 2021/0282659 A1 | 9/2021 | Govari et al. | |
| 2021/0307815 A1 | 10/2021 | Govari et al. | |
| 2021/0308424 A1 | 10/2021 | Beeckler et al. | |
| 2021/0338319 A1 | 11/2021 | Govari et al. | |
| 2021/0370055 A1 | 12/2021 | Waldhauser et al. | |

FOREIGN PATENT DOCUMENTS

| | | |
|---|---|---|
| EP | 0668740 A1 | 8/1995 |
| EP | 0644738 B1 | 3/2000 |
| EP | 0727183 B1 | 11/2002 |
| EP | 0727184 B1 | 12/2002 |
| EP | 2783651 A1 | 10/2014 |
| EP | 2699151 B1 | 11/2015 |
| EP | 2699152 B1 | 11/2015 |
| EP | 2699153 B1 | 12/2015 |
| EP | 2498706 B1 | 4/2016 |
| EP | 2578173 B1 | 6/2017 |
| EP | 3238645 A1 | 11/2017 |
| EP | 2884931 B1 | 1/2018 |
| EP | 2349440 B1 | 8/2019 |
| EP | 3318211 B1 | 12/2019 |
| EP | 3581135 A1 | 12/2019 |
| EP | 2736434 B1 | 2/2020 |
| EP | 3451962 B1 | 3/2020 |
| EP | 3972510 A1 | 3/2022 |
| WO | 9421167 A1 | 9/1994 |
| WO | 9421169 A1 | 9/1994 |
| WO | 9625095 A1 | 8/1996 |
| WO | 9634560 A1 | 11/1996 |
| WO | 0182814 B1 | 5/2002 |
| WO | 2004087249 A2 | 10/2004 |
| WO | 2012100185 A2 | 7/2012 |
| WO | 2013052852 A1 | 4/2013 |
| WO | 2013162884 A1 | 10/2013 |

(56) References Cited

FOREIGN PATENT DOCUMENTS

| WO | 2013173917 A1 | 11/2013 |
| WO | 2013176881 A1 | 11/2013 |
| WO | 2014176205 A1 | 10/2014 |
| WO | 2016019760 A1 | 2/2016 |
| WO | 2016044687 A1 | 3/2016 |
| WO | 2018111600 A1 | 6/2018 |
| WO | 2018191149 A1 | 10/2018 |
| WO | 2019084442 A1 | 5/2019 |
| WO | 2019143960 A1 | 7/2019 |
| WO | 2020026217 A1 | 2/2020 |
| WO | 2020206328 A1 | 10/2020 |
| WO | WO-2021126980 A1 * | 6/2021 ......... A61B 18/1492 |

* cited by examiner

*700*

Start

Form spine assembly *702*

Form electrodes on surface of spine assembly *704*

Form electrical leads on surface of spine assembly *706*

Attach opposite ends of the spine assembly to each other to form a cylindrical basket assembly *708*

Attach cylindrical basket assembly to tubular shaft *710*

End

SYSTEMS AND METHODS FOR CYLINDRICAL CAGE MAPPING AND ABLATION CATHETERS HAVING INTEGRATED ELECTRODES

CROSS REFERENCE TO RELATED APPLICATIONS

This application claims the benefit of priority under 35 U.S.C. § 119 to prior filed U.S. Provisional Patent Application No. 63/477,773, filed Dec. 29, 2022, the entire contents of which is hereby incorporated by reference as if set forth in full herein.

FIELD

The present invention relates generally to medical devices, and in particular to basket catheters comprising a generally cylindrical structure having electrodes attached thereto.

BACKGROUND

Cardiac arrhythmias, such as atrial fibrillation (AF), occur when regions of cardiac tissue abnormally conduct electrical signals to adjacent tissue. This disrupts the normal cardiac cycle and causes asynchronous rhythm. Certain procedures exist for treating arrhythmia, including surgically disrupting the origin of the signals causing the arrhythmia and disrupting the conducting pathway for such signals. By selectively ablating cardiac tissue by application of energy via a catheter, it is sometimes possible to cease or modify the propagation of unwanted electrical signals from one portion of the heart to another.

Many current ablation approaches in the art utilize radiofrequency (RF) electrical energy to heat tissue. RF ablation can have certain risks related to thermal heating which can lead to tissue charring, burning, steam pop, phrenic nerve palsy, pulmonary vein stenosis, and esophageal fistula.

Cryoablation is an alternative approach to RF ablation that generally reduces thermal risks associated with RF ablation. Maneuvering cryoablation devices and selectively applying cryoablation, however, is generally more challenging compared to RF ablation; therefore cryoablation is not viable in certain anatomical geometries which may be reached by electrical ablation devices.

Some ablation approaches use irreversible electroporation (IRE) to ablate cardiac tissue using nonthermal ablation methods. IRE delivers short pulses of high voltage to tissues and generates an unrecoverable permeabilization of cell membranes. Delivery of IRE energy to tissues using multielectrode catheters was previously proposed in the patent literature. Examples of systems and devices configured for IRE ablation are disclosed in U.S. Patent Pub. Nos. 2021/0169550A1 (now U.S. Pat. No. 11,660,135), 2021/0169567A1, 2021/0169568A1, 2021/0161592A1 (now U.S. Pat. No. 11,540,877), 2021/0196372A1, 2021/0177503A1, and 2021/0186604A1 (now U.S. Pat. No. 11,707,320), each of which are incorporated herein by reference and attached in the appendix to priority application U.S. 63/477,773.

Basket catheters are commonly used for mapping or ablating cardiac tissue. For example, basket catheters are described in U.S. Pat. Nos. 5,772,590, 6,748,255 and 6,973,340, each of which are incorporated herein by reference and attached in the appendix to priority application U.S. 63/477,773. Basket catheters generally include a plurality of spines attached to the distal end of the catheter and configured to form a generally spherical shape. Each spine typically has at least one electrode attached thereto configured for mapping or ablation of tissue. Manufacturing basket catheters can be a difficult and expensive process due to the small size and complex geometry. In particular, attaching electrodes to the spines can be difficult, time consuming, and expensive. Accordingly, there is a need in the art for improved methods of manufacturing basket catheters.

An example mapping and ablation procedure with a basket catheter can include bringing a basket catheter into contact with tissue (e.g., cardiac tissue) and detecting electrical signals at the tissue to map the electrical signals across the tissue and/or delivering electrical energy to the electrodes to ablate the tissue. Because of the spherical configuration of the basket catheter, spherical basket catheters tend to be well-suited for ablating rounded geometries, such as the pulmonary vein (e.g., for pulmonary vein isolation), but less effective at mapping electrical pulses across planar tissue surface. Therefore, in some instances, multiple catheters must be used to map and/or ablate tissue in a heart. As will be appreciated, using multiple catheters requires the physician to insert and manipulate the multiple catheters, resulting in longer surgical times. Thus, there is a need in the art for catheter designs capable of performing ablation and mapping of planar tissue as well as rounded tissues, such as a pulmonary vein.

SUMMARY

There is provided in an example of the present disclosure a structural unit for an end effector comprising a proximal member extending along a longitudinal axis. The proximal member can define a plurality of divergent curvilinear members. Each divergent curvilinear member can define two meander members extending along the longitudinal axis such that the structural unit comprises a plurality of meander members. Each of the plurality of meander members can be connected to a respective convergent curvilinear member of a plurality of convergent curvilinear members. The structural unit can further comprise a distal member connected to the plurality of convergent curvilinear members.

The present disclosure includes an end effector for a medical probe. The end effector can comprise a plurality of structural members connected to each other and forming a generally cylindrical structure. Each structural member of the plurality of structural members can comprise a proximal member extending along a longitudinal axis. The proximal member can define a plurality of divergent curvilinear members. Each divergent curvilinear member can define two meander members extending along the longitudinal axis such that the structural member comprises a plurality of meander members. Each of the plurality of meander members can be connected to a respective convergent curvilinear member of a plurality of convergent curvilinear members. The end effector can further include a distal member connected to the plurality of convergent curvilinear members.

The present disclosure includes a structural unit for an end effector comprising a proximal member extending along a longitudinal axis, a first divergent curvilinear member connected to a distal end of the proximal member, a second divergent curvilinear member connected to the distal end of the proximal member, a first meander member connected to a distal end of the first divergent curvilinear member, a second meander member connected to the distal end of the first divergent curvilinear member, a third meander member connected to a distal end of the second divergent curvilinear member, a fourth meander member connected to the distal end of the second divergent curvilinear member, a first convergent curvilinear member, the first meander member and the second meander member being connected to the first convergent curvilinear member, and a second convergent curvilinear member. The third meander member and the fourth meander member can be connected to the second convergent curvilinear member. The structural unit can further comprise a distal member connected to the first convergent curvilinear member and the second convergent curvilinear member.

The present disclosure includes a method of constructing a medical probe. The method can comprise forming a plurality of spines from a planar sheet of material, forming a plurality of electrodes on the planar sheet of material by vacuum deposition, and forming a plurality of electrical traces on the planar sheet of material. Each electrical trace of the plurality of electrical traces can be connected to a respective electrode of the plurality of electrodes. The method can include connecting opposite ends of the planar sheet of material to each other to form a cylindrical structure.

BRIEF DESCRIPTION OF THE DRAWINGS

The present disclosure will be more fully understood from the following detailed description of the examples thereof, taken together with the drawings in which:

FIG. 5A is a schematic pictorial illustration of a plurality of spines in a collapsed form while

FIG. 6A is a schematic pictorial illustration showing a side view of a basket assembly in an expanded form while

DETAILED DESCRIPTION

Figure 1:
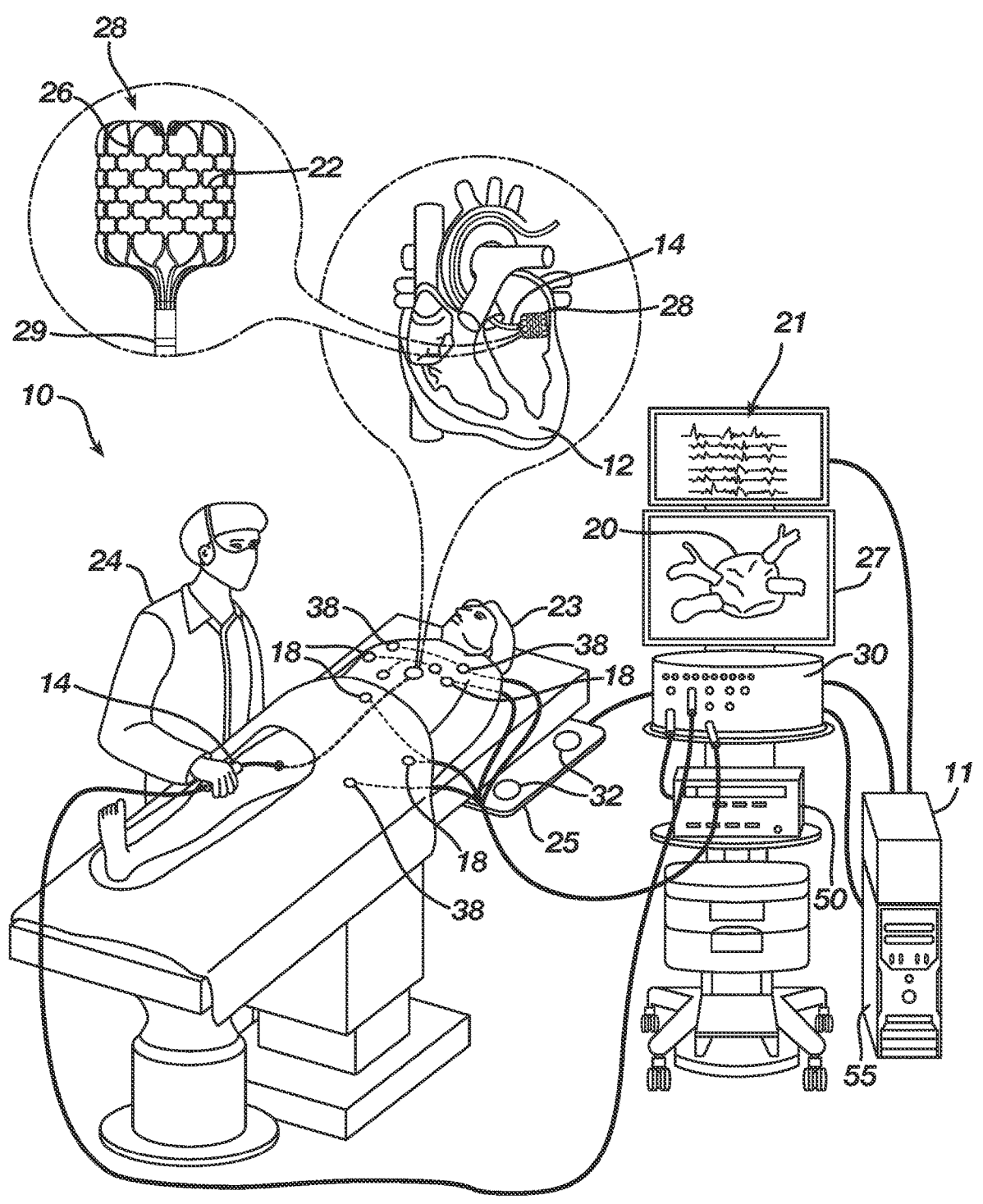
FIG. 1 is a schematic pictorial illustration of a medical system including a medical probe whose distal end includes a basket assembly with electrodes, in accordance with an example of the present invention.

As will become apparent throughout this disclosure, the disclosed technology includes several advantages over the prior art. The disclosed technology can include an expandable basket assembly having a generally cylindrical shape. The expandable basket assembly can have a plurality of electrodes attached thereto that can be configured for mapping or ablation of tissue. By including an expandable basket assembly having a generally cylindrical shape, the disclosed technology can be well suited for mapping or ablating generally planar tissue as well as generally circularly-shaped tissue, such as a pulmonary vein. For instance, the generally cylindrical shape can have an approximately planar end having electrodes disposed thereon for mapping or ablating generally planar tissue. The generally cylindrical shape can further include electrodes disposed around an outer circumferential surface that can be configured to mapping or ablating generally circularly-shaped tissue.

The disclosed technology can include electrodes formed directly onto the spines which form the expandable basket assembly. The electrodes can be formed directly onto the spines using vacuum deposition such as physical vapor deposition or chemical vapor deposition. In other words, the process of manufacturing a basket catheter can be simplified because the electrodes are formed directly onto the spine rather than formed separately from the spine and later attached to the spine.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 110%.

As used herein, the terms "patient," "host," "user," and "subject" refer to any human or animal subject and are not intended to limit the systems or methods to human use, although use of the subject invention in a human patient represents a preferred embodiment. In addition, vasculature of a "patient," "host," "user," and "subject" can be vasculature of a human or any animal. It should be appreciated that an animal can be a variety of any applicable type, including, but not limited thereto, mammal, veterinarian animal, livestock animal or pet type animal, etc. As an example, the animal can be a laboratory animal specifically selected to have certain characteristics similar to a human (e.g., rat, dog, pig, monkey, or the like). It should be appreciated that the subject can be any applicable human patient, for example. As well, the term "proximal" indicates a location closer to the operator or physician whereas "distal" indicates a location further away to the operator or physician.

As discussed herein, "physician" can include a doctor, surgeon, technician, scientist, operator, or any other individual or delivery instrumentation associated with delivery of a multi-electrode catheter for the treatment of drug refractory atrial fibrillation to a subject.

As used herein, the term "meander" refers to a periodic or repeating pattern of structural elements oriented about a center line. A number designating a meander (e.g., a "first meander" or "second meander") is meant to identify and differentiate two or more different patterns. The two or more different patterns can be the same or similar type of pattern, a mirror image of patterns, or entirely different types of patterns depending on the configuration.

As discussed herein, the term "ablate" or "ablation", as it relates to the devices and corresponding systems of this disclosure, refers to components and structural features configured to reduce or prevent the generation of erratic cardiac signals in the cells by utilizing thermal energy such as RF ablation or cryoablation, or non-thermal energy, such as irreversible electroporation (IRE), referred throughout this disclosure interchangeably as pulsed electric field (PEF) and pulsed field ablation (PFA). IRE ablation can include monophasic or biphasic pulses. Furthermore, the disclosed technology can include reversible electroporation.

Ablating or ablation as it relates to the devices and corresponding systems of this disclosure is used throughout this disclosure in reference to non-thermal ablation of cardiac tissue for certain conditions including, but not limited to, arrhythmias, atrial flutter ablation, pulmonary vein isolation, supraventricular tachycardia ablation, and ventricular tachycardia ablation. The term "ablate" or "ablation" also includes known methods, devices, and systems to achieve various forms of bodily tissue ablation as understood by a person skilled in the relevant art.

As discussed herein, the terms "tubular" and "tube" are to be construed broadly and are not limited to a structure that is a right cylinder or strictly circumferential in cross-section or of a uniform cross-section throughout its length. For example, the tubular structures are generally illustrated as a substantially right cylindrical structure. However, the tubular structures may have a tapered or curved outer surface without departing from the scope of the present disclosure.

The present disclosure is related to systems, methods or uses and devices which utilize end effectors including cylindrical basket catheters having electrodes directly formed onto the spines. Example systems, methods, and devices of the present disclosure may be particularly suited for mapping and ablation of cardiac tissue to treat cardiac arrhythmias. Ablative procedures incorporating such example catheters can be visualized using fluoroscopy.

Reference is made to FIG. 1, showing an example catheter-based electrophysiology mapping and ablation system 10. System 10 includes multiple catheters, which are percutaneously inserted by physician 24 through the patient's 23 vascular system into a chamber or vascular structure of a heart 12. Typically, a delivery sheath catheter is inserted into the left or right atrium near a desired location in heart 12. Thereafter, a plurality of catheters can be inserted into the delivery sheath catheter so as to arrive at the desired location. The plurality of catheters may include catheters dedicated for sensing Intracardiac Electrogram (IEGM) signals, catheters dedicated for ablating and/or catheters dedicated for both sensing and ablating. An example catheter 14 that is configured for sensing IEGM is illustrated herein. Physician 24 brings a distal tip (basket assembly 28) of catheter 14 comprising a medical probe 16 into contact with the heart wall at or near the pulmonary vein for sensing a target site in heart 12. For ablation, physician 24 would similarly bring a distal end of an ablation catheter comprising medical probe 16 to a target site for ablating.

Medical probe 16 is an exemplary probe that includes one and preferably multiple electrodes 26 optionally distributed over a plurality of spines 22 at basket assembly 28 and configured to sense the IEGM signals. Medical probe 16 may additionally include a position sensor 29 embedded in or near basket assembly 28 for tracking position and orientation of basket assembly 28. Optionally and preferably, position sensor 29 is a magnetic based position sensor (e.g., an electromagnetic coil) including three magnetic coils for sensing three-dimensional (3D) position and orientation. Position sensor 29 can be conventional coiled wire sensors, flat PCB based sensors, or deformable electromagnetic loop sensors. Although not depicted, position sensor 29 can alternatively be positioned on the basket assembly 28 or designed into individual spines 22. In some embodiments, individual spines 22 can be insulated and act as a position sensor.

In some embodiments, medical probe 16 can include a deformable electromagnetic loop sensor. Examples of various systems and methods for deformable electromagnetic loop sensors are presented in U.S. Pat. Nos. 11,304,642 and 10,330,742, and U.S. Patent Publications 2018/0344202A1 and 2020/0155224A1, each of which are incorporated herein by reference and attached in the appendix to priority application U.S. 63/477,773.

Magnetic based position sensor 29 may be operated together with a location pad 25 including a plurality of magnetic coils 32 configured to generate magnetic fields in a predefined working volume. Real time position of basket assembly 28 of catheter 14 may be tracked based on magnetic fields generated with location pad 25 and sensed by magnetic based position sensor 29. Details of the magnetic based position sensing technology are described in U.S. Pat. Nos. 5,391,199; 5,443,489; 5,558,091; 6,172,499; 6,239, 724; 6,332,089; 6,484,118; 6,618,612; 6,690,963; 6,788, 967; 6,892,091, each of which are incorporated herein by reference and attached in the appendix to priority application U.S. 63/477,773.

System 10 includes one or more electrode patches 38 positioned for skin contact on patient 23 to establish location reference for location pad 25 as well as impedance-based tracking of electrodes 26. For impedance-based tracking, electrical current is directed toward electrodes 26 and sensed at electrode skin patches 38 so that the location of each electrode can be triangulated via the electrode patches 38. Details of the impedance-based location tracking technology are described in U.S. Pat. Nos. 7,536,218; 7,756,576; 7,848, 787; 7,869,865; and 8,456,182, each of which are incorporated herein by reference and attached in the appendix to priority application U.S. 63/477,773.

A recorder 11 displays electrograms 21 captured with body surface ECG electrodes 18 and intracardiac electrograms (IEGM) captured with electrodes 26 of catheter 14. Recorder 11 may include pacing capability for pacing the heart rhythm and/or may be electrically connected to a standalone pacer.

System 10 may include an ablation energy generator 50 that is adapted to conduct ablative energy to one or more of electrodes at a distal tip of a catheter configured for ablating. Energy produced by ablation energy generator 50 may include, but is not limited to, radiofrequency (RF) energy or pulsed-field ablation (PFA) energy, including monopolar or bipolar high-voltage DC pulses as may be used to effect irreversible electroporation (IRE), or combinations thereof.

Patient interface unit (PIU) 30 is an interface configured to establish electrical communication between catheters, electrophysiological equipment, power supply and a workstation 55 for controlling operation of system 10. Electrophysiological equipment of system 10 may include for example, multiple catheters, location pad 25, body surface ECG electrodes 18, electrode patches 38, ablation energy generator 50, and recorder 11. Optionally and preferably, PIU 30 additionally includes processing capability for implementing real-time computations of location of the catheters and for performing ECG calculations.

Workstation 55 includes memory, processor unit with memory or storage with appropriate operating software loaded therein, and user interface capability. Workstation 55 may provide multiple functions, optionally including (1) modeling the endocardial anatomy in three-dimensions (3D) and rendering the model or anatomical map 20 for display on a display device 27, (2) displaying on display device 27 activation sequences (or other data) compiled from recorded electrograms 21 in representative visual indicia or imagery superimposed on the rendered anatomical map 20, (3) displaying real-time location and orientation of multiple catheters within the heart chamber, and (4) displaying on display device 27 sites of interest such as places where ablation energy has been applied. One commercial product embodying elements of the system 10 is available as the CARTO™ 3 System, available from from Biosense Webster, Inc., 31 Technology Drive, Suite 200, Irvine, CA 92618 USA.

Figure 2:
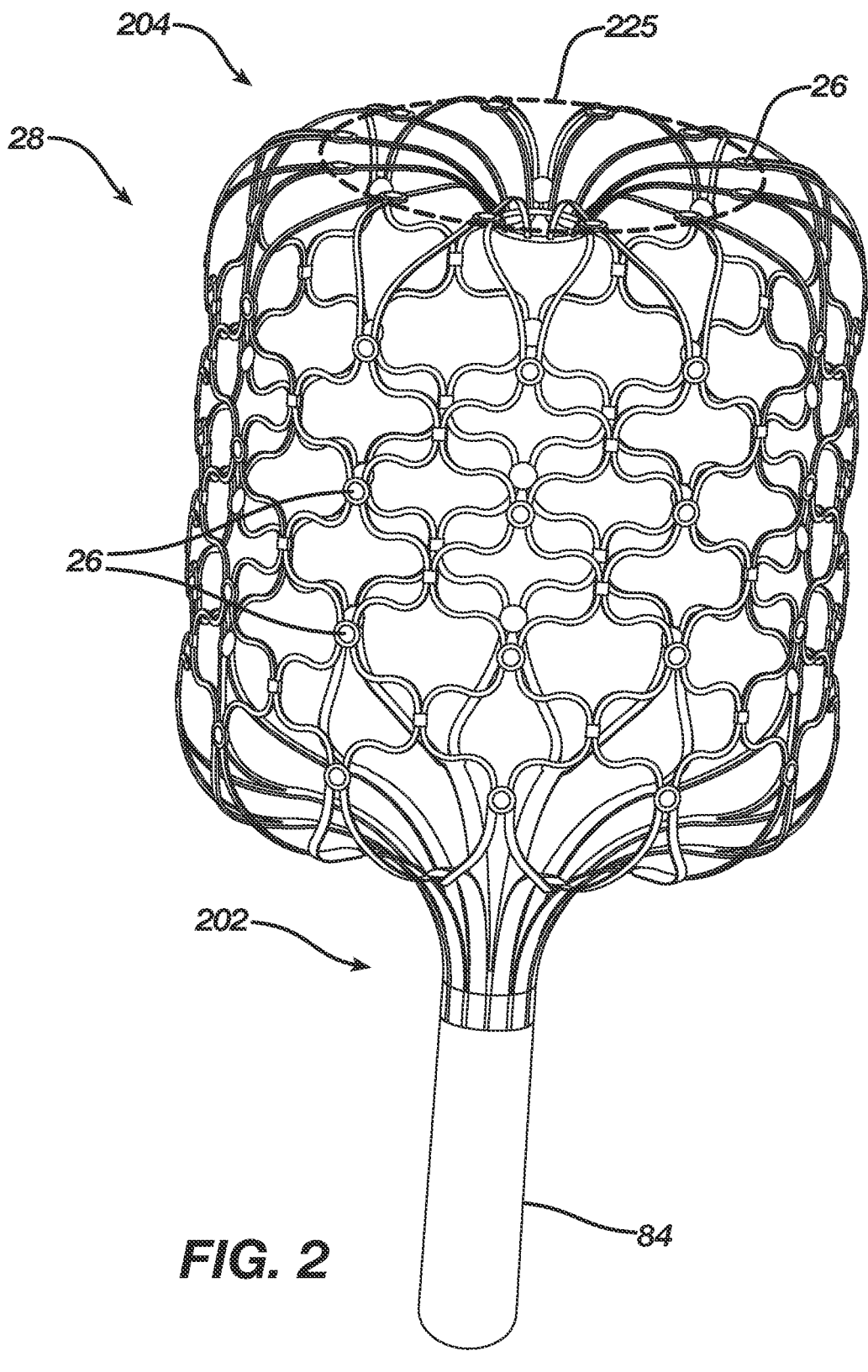
FIG. 2 is a schematic pictorial illustration showing a perspective view of a basket assembly in an expanded form, in accordance with an embodiment of the present invention.
Figure 3A:
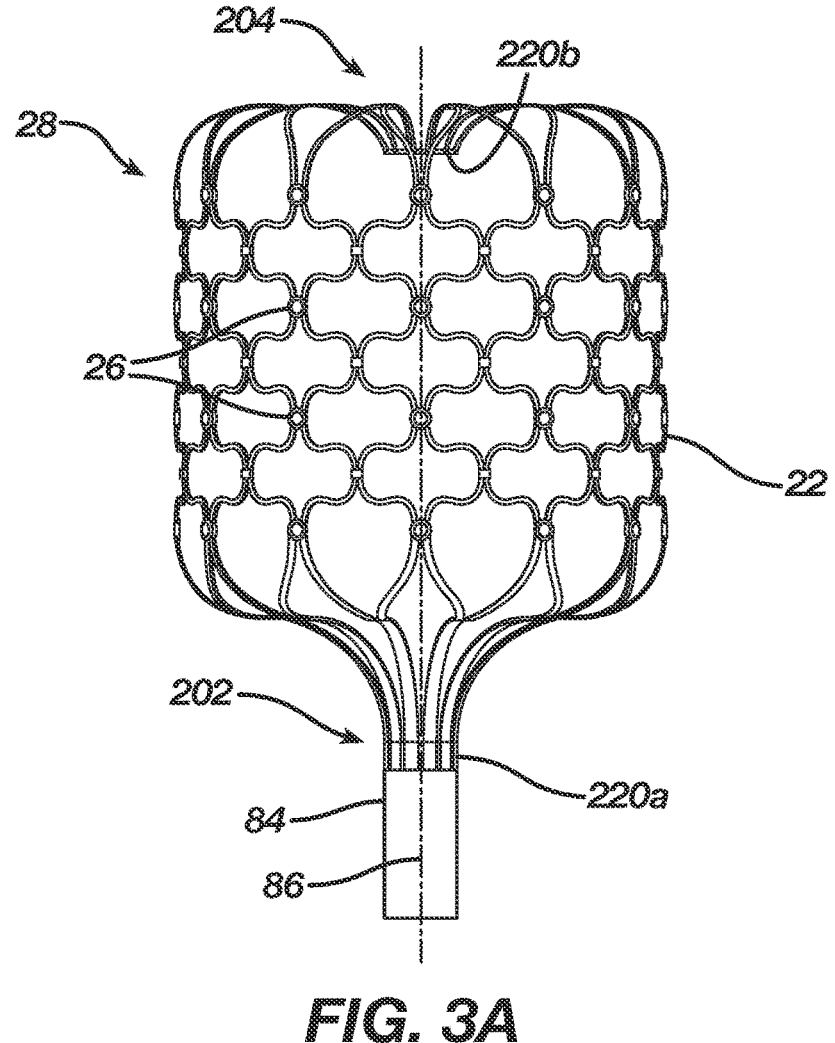
FIG. 3A is a schematic pictorial illustration showing a side view of a basket assembly in an expanded form, in accordance with the disclosed technology.
Figure 3B:
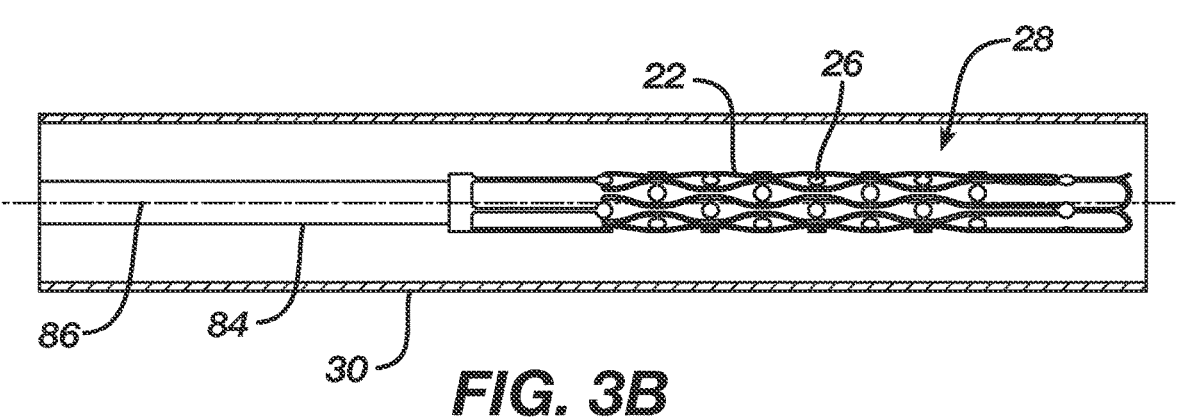
FIG. 3B is a schematic pictorial illustration showing a side view of a basket assembly in a collapsed form, in accordance with the disclosed technology.

FIG. 2 is a schematic pictorial illustration showing a perspective view of a medical probe 200 in an expanded form while FIG. 3A is a schematic pictorial illustration showing a side view of the medical probe 200 in the expanded form, in accordance with the disclosed technology. The medical probe 200 can be in an expanded form when unconstrained, such as by being advanced out of a delivery sheath 80 by a tubular shaft 84. FIG. 3B, on the other hand, is a schematic pictorial illustration showing a side view of the medical probe 200 in a collapsed form, such as by being retracted into the delivery sheath 80. In the expanded form (FIGS. 2 and 3A), the spines 22 bow radially outwardly along a longitudinal axis 86 and in the collapsed form (FIG. 2B) the spines are constrained generally along the longitudinal axis 86 of tubular shaft 84.

As shown in FIGS. 2 and 3A, the medical probe 200 can include a basket assembly 28 comprising a plurality of flexible spines 22 that are formed at the end of a tubular shaft 84 and are connected at both ends. During a medical procedure, physician 24 can deploy basket assembly 28 by extending tubular shaft 84 from delivery sheath 80 causing the basket assembly 28 to exit the delivery sheath 80 and transition to the expanded form.

As shown in FIGS. 2 and 3A, the basket assembly 28 can include a proximal end 202 and a distal end 204 and form a generally cylindrical shape. The spines 22 can extend between a proximal hub 220a and a distal hub 220b to which the spines 22 can be connected. The distal end 204 can include a generally planar portion 225. As will be described in greater detail herein, the basket assembly 28 can include a plurality of electrodes 26 formed onto the spine 22. Due to the cylindrical shape of the basket assembly 28, the medical probe 200 described herein can be configured for mapping and/or ablation of both planar tissue (e.g., generally planar surfaces of a heart) and rounded tissue locations (e.g., a pulmonary vein). In this way, the medical probe 200 can be configured to perform mapping and/or ablation of multiple surfaces of an organ in a single procedure without requiring the use of multiple catheters having different end effector shapes. The planar portion 225, for example, can have a plurality of electrodes 26 disposed thereon configured for mapping and/or ablation of generally planar tissue and the sides of the cylindrical structure of the basket assembly 28 can include a plurality of electrodes 26 disposed thereon configured for mapping and/or ablation of generally rounded tissue location. The electrodes 26, for example, can be configured to deliver pulses for irreversible electroporation (IRE) with the pulses having a peak voltage of at least 900 volts.

The basket assembly 28 can be formed from a planar sheet of biocompatible material or a cylindrical stock of biocompatible material. For example, the spines 22 can be cut into the biocompatible material and then the basket assembly 28 can be formed into the cylindrical shape by heat setting or otherwise causing the spines 22 to retain the cylindrical shape. The biocompatible material can be any suitable type of biocompatible material including, but not limited to, nitinol, stainless steel, cobalt chromium, polymer material, or other suitable materials.

Figure 4A:
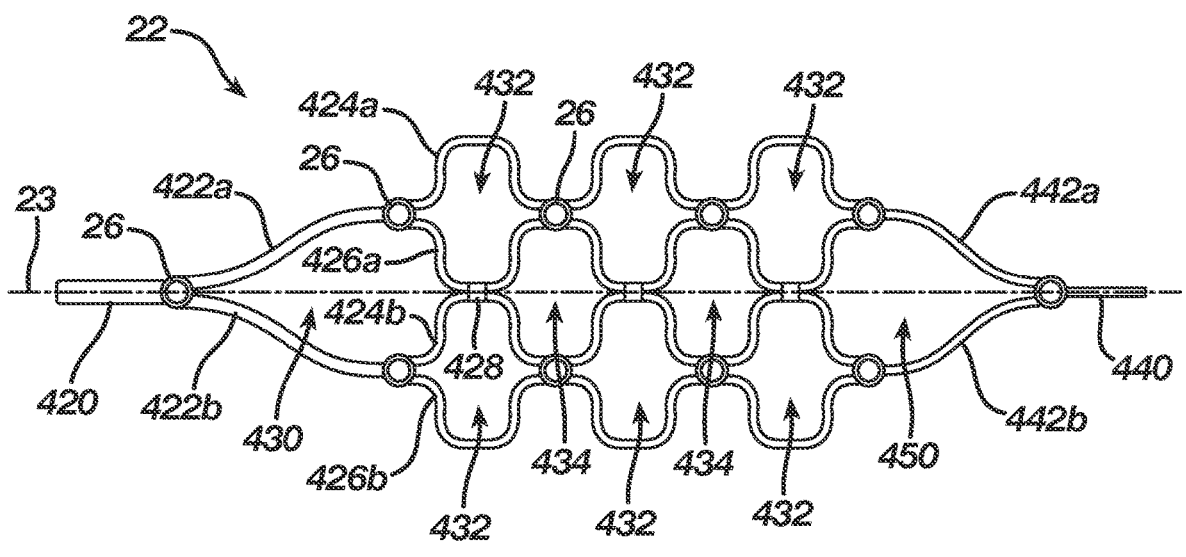
FIG. 4A is a schematic pictorial illustration showing a spine of a basket assembly, in accordance with the disclosed technology.
Figure 4B:
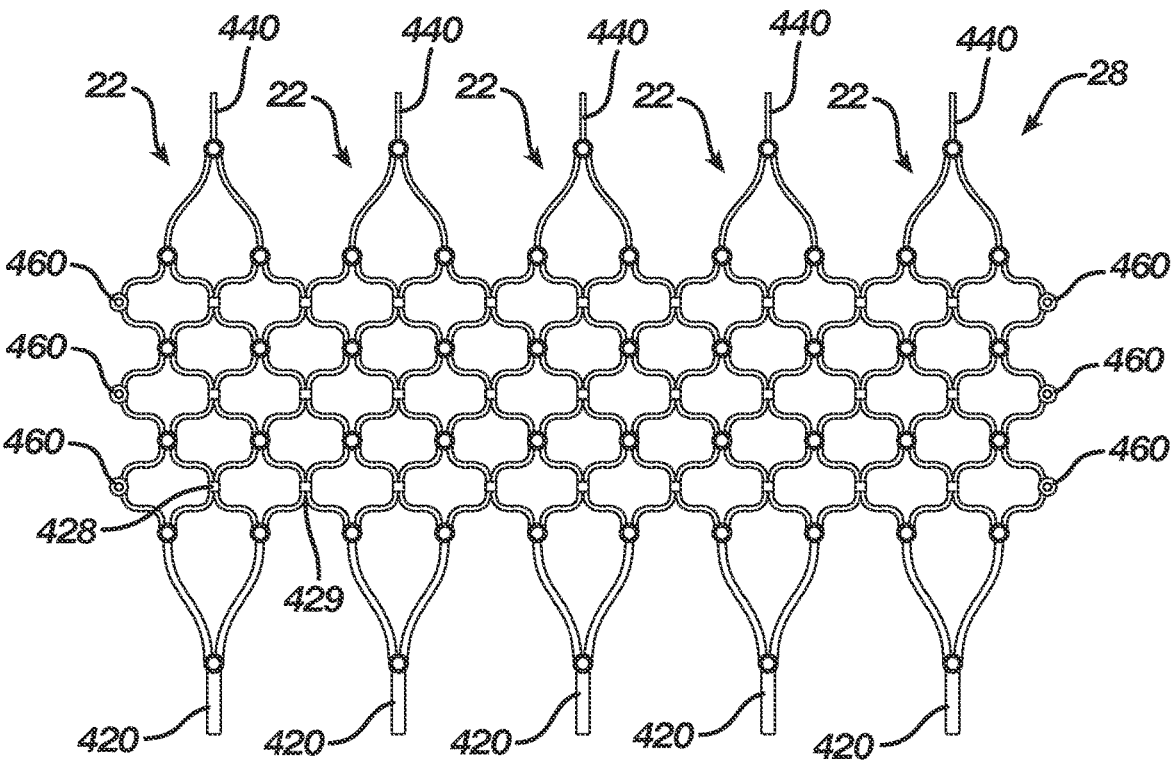
FIGS. 4B and 4C are schematic pictorial illustrations of a plurality of spines connected together, in accordance with examples of the disclosed technology.

FIG. 4A is a schematic pictorial illustration showing a spine 22 of the medical probe 200, in accordance with the disclosed technology. As will be appreciated, the basket assembly 28 can be made up of several spines 22 connected together. Each spine 22 can have a similar curvilinear shape or pattern as that illustrated in FIG. 4A. Several spines 22 can be connected together to form an array of spines as shown in FIG. 4B. Spines 22 at either end of the array can include connection points 460 which can be connected together to form a generally cylindrical shape. The spine 22 can include a proximal member 420 and a distal member 440. The proximal member 420 can be connected to the proximal hub 220a and the distal member 440 can be connected to the distal hub 420b to form the generally cylindrically-shaped basket assembly 28 shown in FIGS. 2-3B.

As shown in FIG. 4A, and moving from left to right in the figure, the spine 22 can include a proximal member 420 that can be configured for attachment to a proximal hub 220a as just described. The spine 22 can further include a first divergent curvilinear member 422a and a second divergent curvilinear member 422b that can be attached to the proximal member 420 and diverge outwardly from the proximal member 420. Each divergent curvilinear member 422a, 422b can be attached to a first meander member 424a, 424b and a second meander member 426a, 426b that can each form a shape having a repeating pattern as shown in FIG. 4A. The first meander members 424a, 424b and the second meander members 426a, 426b can, for example, form a generally sinusoidal pattern extending generally distally between the respective first divergent curvilinear member 422a and the second divergent curvilinear member 422b and a first convergent curvilinear member 442a and a second convergent curvilinear member 442b. The pattern can be repeated only once or the pattern can be repeated a plurality of times between the respective first and second divergent curvilinear member 422a, 422b and the respective first and second convergent curvilinear member 442a, 442b. For example, the pattern can be repeated once, twice, three times (as shown in FIG. 4A), four times, five times, ten times, twenty times, or any other number of times as would be suitable for the particular configuration. Each meander member 424a, 424b, 426a, 426b can have generally curved turns as shown in FIG. 4A. Alternatively, each meander member 424a, 424b, 426a, 426b can have generally angled or squared turns. The first convergent curvilinear member 442a and the second convergent curvilinear member 442b can each converge toward, and be attached to, a distal member 440.

The spine 22 can be connected at intersections 428 where the second meander member 426a and the first meander member 424b touch as shown in FIG. 4A. In this way, the spine 22 can form a unitary structure and be structurally strengthened. The intersections 428 can be positioned approximately in line with a centerline 23 of the spine 22.

The spine 22 can define various cells at locations between portions of the spine 22. As shown, a proximal cell 430 can be positioned between the first and second divergent curvilinear member 422a, 422b and the second meander member 426a and the first meander member 424b. Similarly, a distal cell 450 can be positioned between the second meander member 426a and the first meander member 424b and the first and second convergent curvilinear members 442a, 442b. Furthermore, intermediary cells 432 can be positioned between first and second meander members 424a, 426a and first and second meander members 424b, 426b.

As shown in FIG. 4A, the spine 22 can have a plurality of electrodes 26 attached thereto at various intersections or points between each member. For example, an electrode 26 can be attached to the spine 22 at a point between the proximal member 420 and the first and second divergent curvilinear member 422a, 422b. Electrodes 26 can be positioned at locations between the respective first and second divergent curvilinear member 422a, 422b and the respective first and second meander members 424a, 424b, 426a, 426b. Electrodes 26 can be positioned between the first and second meander members 424a, 426a and the first and second meander members 424b, 426b. Electrodes 26 can be positioned between respective first and second meander members 424a, 424b, 426a, 426b and respective convergent curvilinear members 442a, 442b. Electrodes can be attached to the spine at a point between the convergent curvilinear members 442a, 442b and the distal member 440.

Figure 4C:
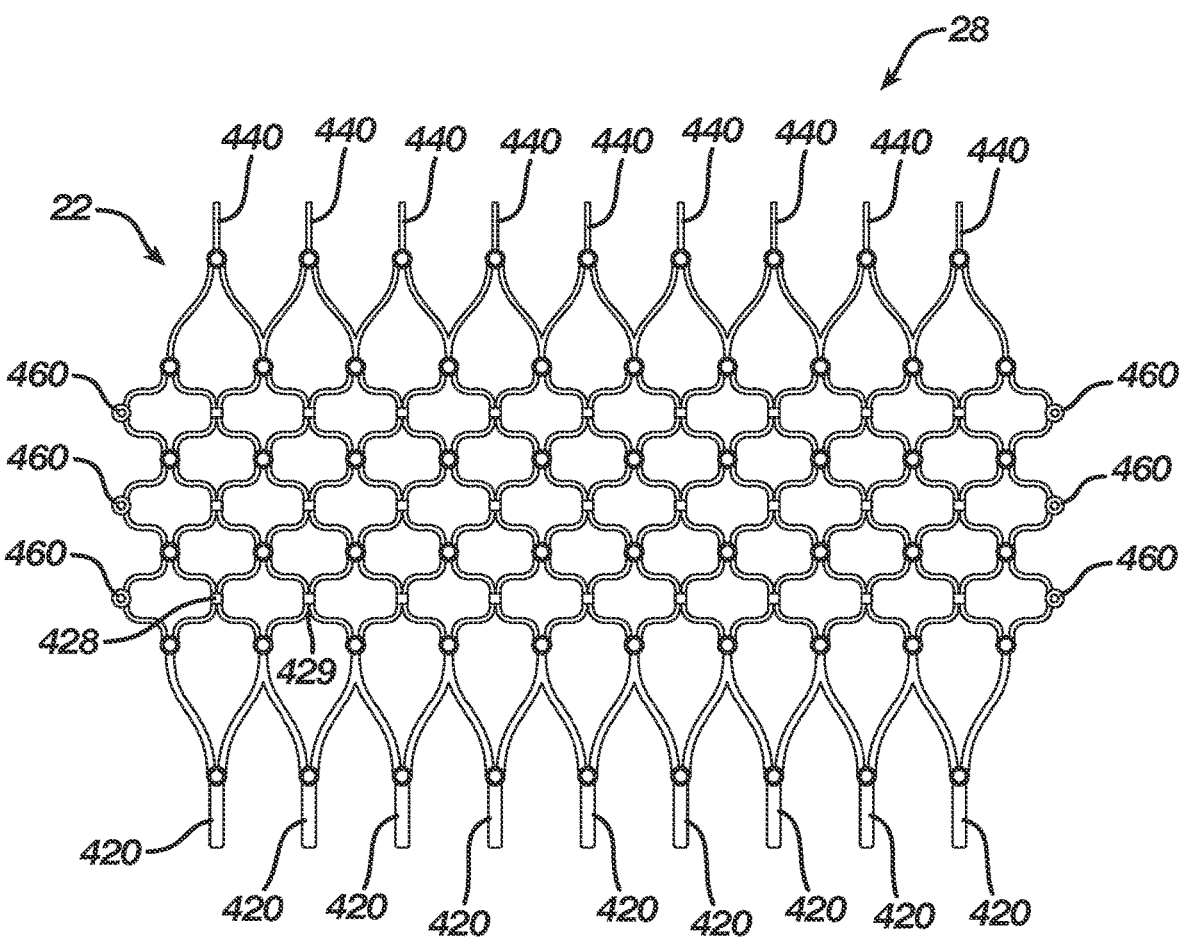

FIGS. 4B and 4C are schematic pictorial illustrations of a plurality of spines 22 connected together, in accordance with examples of the disclosed technology. The spines 22 can be connected together to form the basket 28. As shown, adjoining spines 22 can be connected together at points 429 wherein adjacent first and second meandering members 424a, 426b touch. As will be appreciated, the spines 22 can be cut from a single sheet of biocompatible material. Therefore, the points 429 can be locations where the sheet of biocompatible material was not cut. In other words, the spines 22 can all be formed together as a continuous material rather than cut individually and then later connected together at the points 420. Alternatively, the spines 22 can be cut individually and then later connected together at the points 420. Furthermore, as will be appreciated, the points 429 and the intersections 428 can be substantially similar except for their position on or between the spine 22.

As shown, spines 22 at either end of the assembled spines 22 can include connection points 460 that can be used to connect the ends of the assembled spines 22 together to form the generally cylindrically-shaped basket assembly 28. For example, the spines 22 can all be cut together from a planar sheet of biocompatible material and then the connection points 460 can be aligned with, and connected to, each other to form the basket assembly 28.

As shown in FIG. 4B, the spines 22 can include only a single proximal member 420 and distal member 440 for each individual spine 22 or, as shown in FIG. 4C, the spines 22 can include more than one proximal member 420 and distal member 440 attached to each spine 22. Thus, for the example shown in FIG. 4C, in addition to the points 429, adjoining spines can be connected together via an additional proximal member 420 and distal member 440 and adjoining divergent curvilinear members 422a, 422b and adjoining convergent curvilinear members 442a, 442b.

Figure 5B:
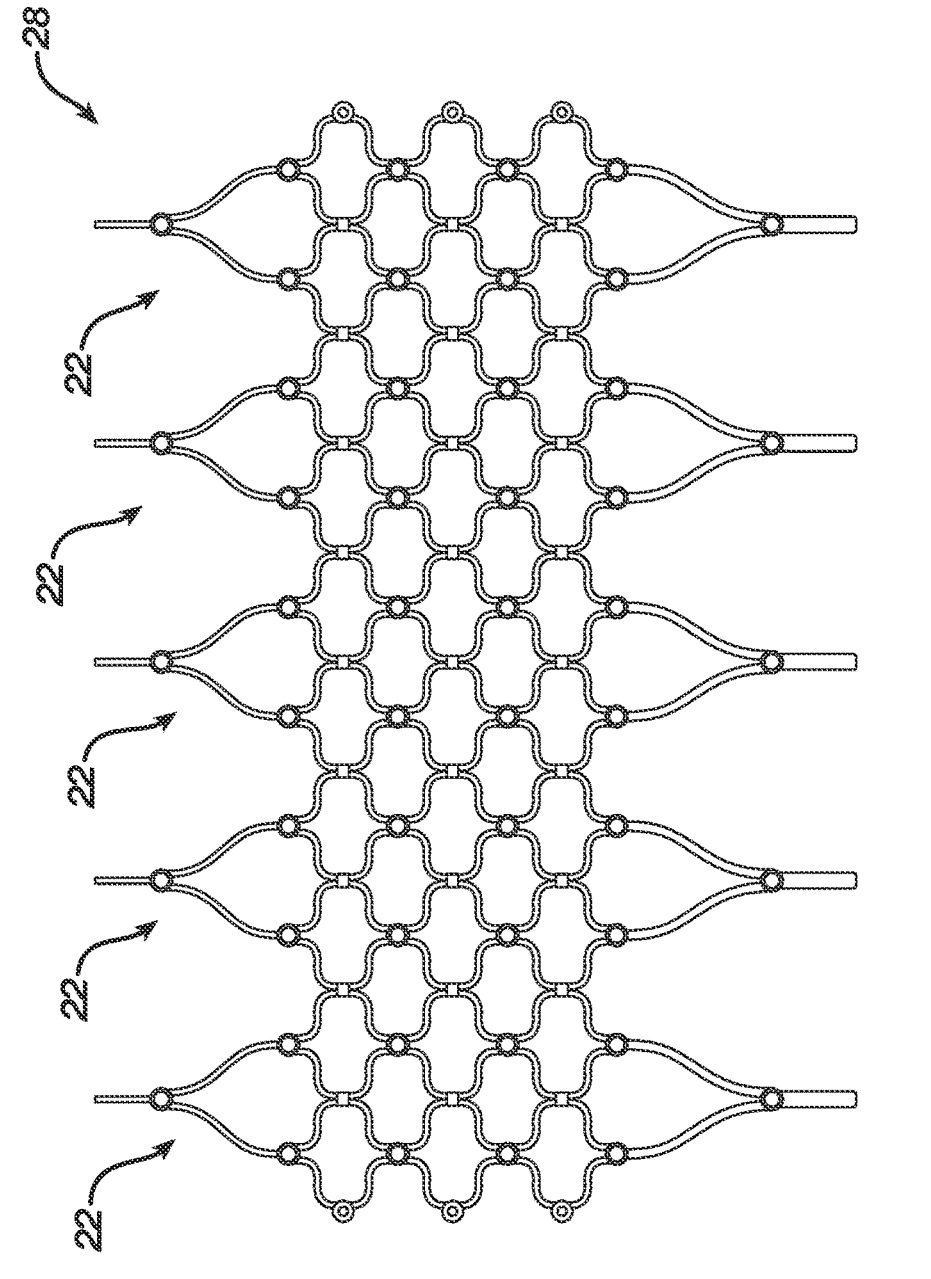
FIG. 5B is a schematic pictorial illustration of a plurality of spines in an expanded form, in accordance with the disclosed technology.
Figure 5A:
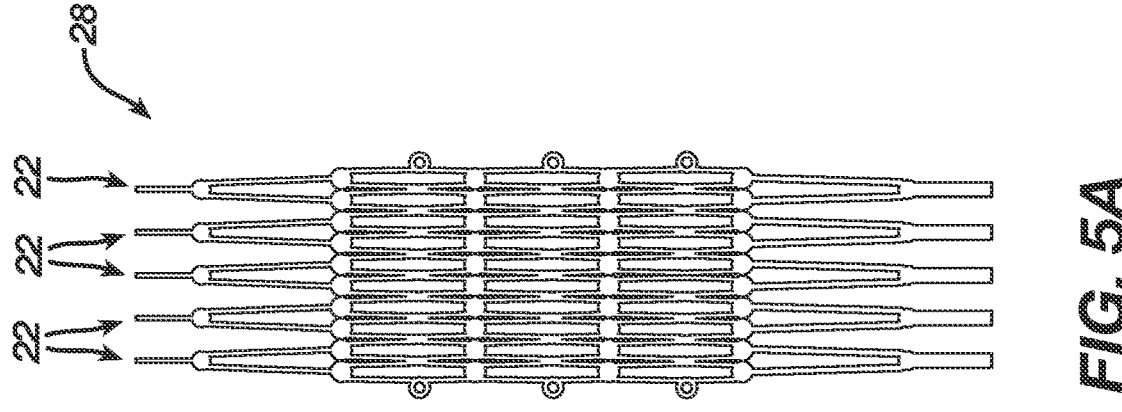

FIG. 5A is a schematic pictorial illustration of a plurality of spines 22 in a collapsed form while FIG. 5B is a schematic pictorial illustration of a plurality of spines 22 in an expanded form, in accordance with the disclosed technology. As described previously, the spines 22 can be cut from a planar sheet of biocompatible material. To reduce material waste, the spines 22 can be cut in the form shown in FIG. 5A and then later stretched or expanded to form the array shown in FIG. 5B.

Figure 6A:
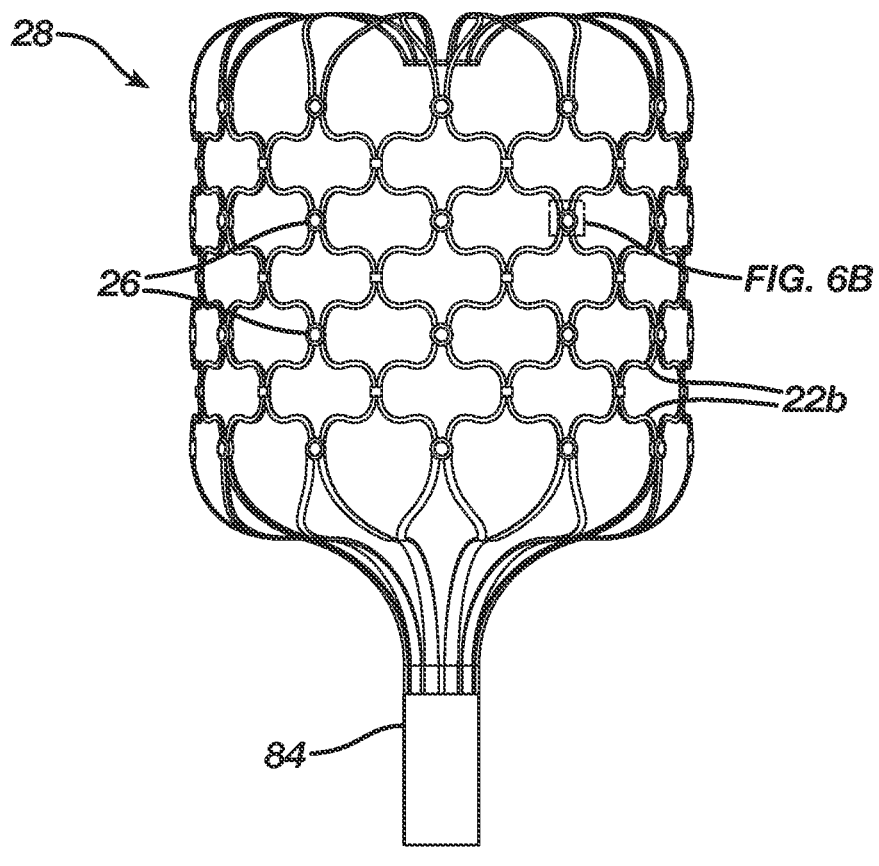
Figure 6B:
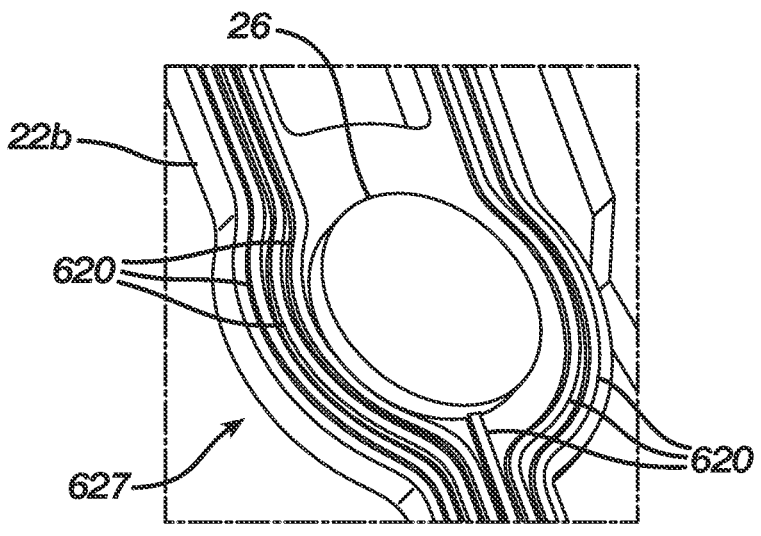
FIG. 6B is a detail view of an electrode on the basket assembly, in accordance with the disclosed technology.

FIG. 6A is a schematic pictorial illustration showing a side view of a basket assembly 28 in an expanded form while FIG. 6B is a detail view of an electrode 26 on the basket assembly 28, in accordance with the disclosed technology. As shown in FIG. 6B, the electrodes 26 can be formed directly onto the spine 22. The electrode 26 can be formed directly onto the spine using, for example, vacuum deposition. The vacuum deposition can include, but is not limited to, physical vapor deposition, chemical vapor deposition, or atomic layer deposition. For vapor deposition, a layer of nitinol can be deposited, followed by a thin insulation layer, and then the conductive trace and electrode layers. As will be appreciated, by forming the electrodes directly onto the spine 22 using vacuum deposition, the disclosed technology can reduce or eliminate many of the complications and errors associated with forming electrodes separate from the spines and then later assembling electrodes onto the spines. In some examples, the electrodes 26 can be formed into the basket assembly by lithography methods, sputtering methods (e.g., spin coating, direct-write sputtering, or sputter coating), printing (e.g., 3D printing), electrodeposition, or photolithography.

The spines 22 can further include electrical leads 620 that can similarly be formed directly onto the spines 22 using vacuum deposition. The electrical leads 620 can be electrically connected to individual electrodes 26 distributed on the spines 22 at various locations. The electrical leads 620 can extend along the length of the spine to the proximal hub 220 where the electrical leads 620 can be electrically connected to wires of the medical probe 17 for sending and/or receiving signals or electrical pulses for mapping and/or ablation.

The basket assembly 28 can include an electrode 26 on a first side of the spine 22 and a reference electrode 627 (on an underside of the spine 22 of FIG. 6B) on a second side of the spine 22. The reference electrode 627 can be configured for receiving far field signals conducted through the blood or other fluid in an organ. As will be appreciated, the far field signals detected by the reference electrode 627 can be received and processed by a computer (e.g., the PIU 30) to compare the signals received from the electrodes 26 to the signals received from the reference electrodes 627 to ensure the signals received for mapping are representative of electrocardiographic signals through the tissue. Reference electrodes that are configured to measure the electrical signals from the fluid and/or blood directly adjacent to an electrode that is touching tissue. As such, the reference electrodes are insulated from touching tissue and the resulting signals collected are non-local far-field signals. The information from this reference electrode can be used to cancel out far-field signal from the adjacent, tissue touching electrode to ensure that the tissue touching electrode collects local information only.

Figure 7:
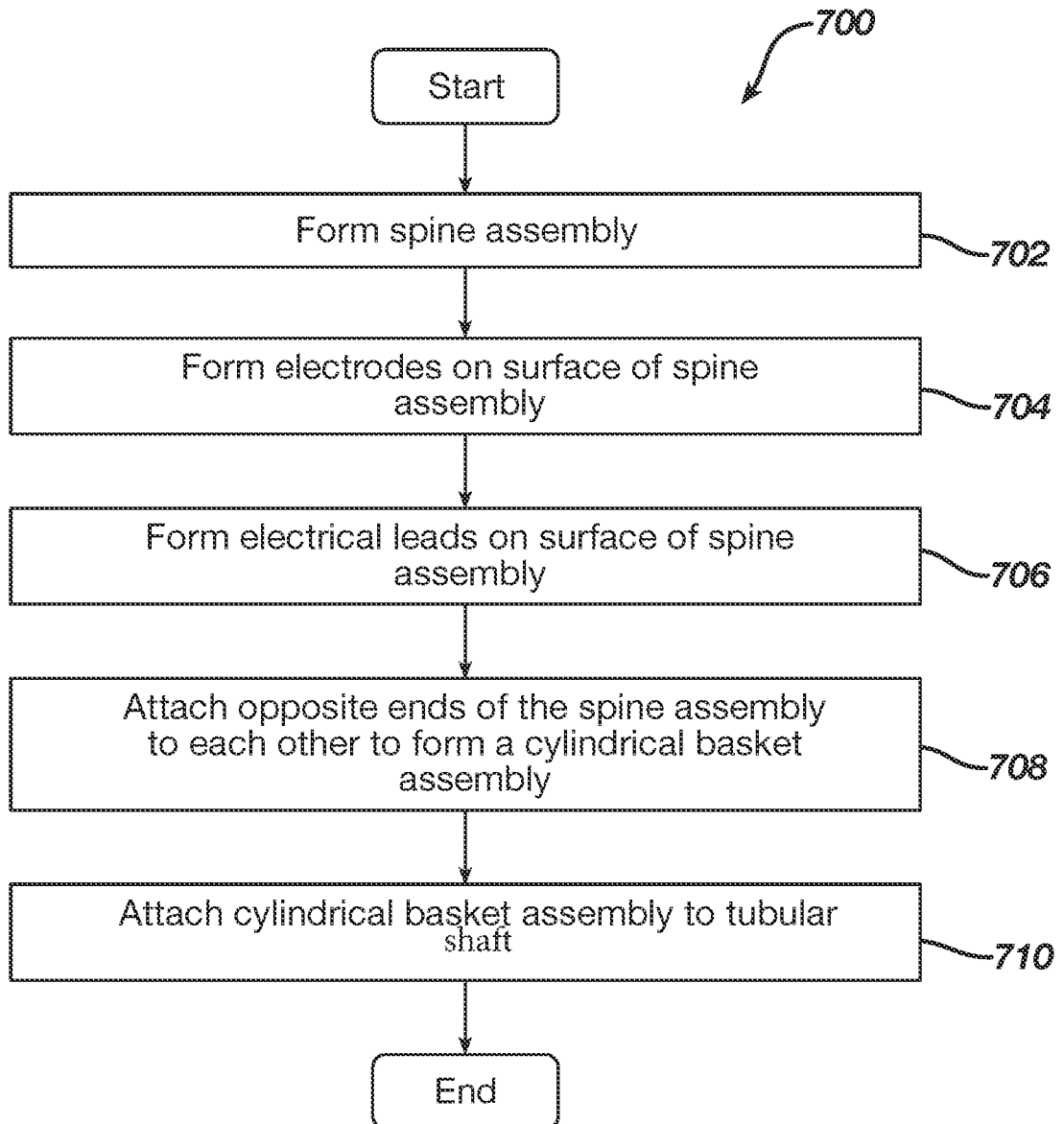
FIG. 7 is a flowchart of a method of manufacturing a medical probe, in accordance with the disclosed technology.

FIG. 7 is a flowchart of a method 700 of manufacturing a medical probe, in accordance with the disclosed technology. The method 700 can include forming a spine assembly from, for example, a planar sheet or cylindrical stock of biocompatible material (step 702). Using, for example, vacuum deposition, the method 700 can include forming electrodes on the surface of the spine assembly and forming 706 electrical leads on the spine assembly (step 704). The method 700 can include attaching opposite ends of the spine assembly to each other to form a cylindrical basket assembly (step 708). The method 700 can further include attaching the cylindrical basket assembly to a tubular shaft to form a generally cylindrically-shaped medical probe (step 710). As will be appreciated, the method 700 just described can include any of the previous examples described herein.

The disclosed technology described herein can be further understood according to the following clauses:

Clause 1: A structural unit for an end effector comprising: a proximal member extending along a longitudinal axis, the proximal member defining a plurality of divergent curvilinear members; each divergent curvilinear member defining two meander members extending along the longitudinal axis such that the structural unit comprises a plurality of meander members, each of the plurality of meander members being connected to a respective convergent curvilinear member of a plurality of convergent curvilinear members; and a distal member connected to the plurality of convergent curvilinear members.

Clause 2: The structural unit according to Clause 1, wherein the plurality of divergent curvilinear members comprises two divergent curvilinear members.

Clause 3: The structural unit according to Clause 1 or 2, wherein the plurality of meander members comprises four meander members.

Clause 4: The structural unit according to any of the preceding Clauses, wherein the plurality of convergent curvilinear members comprises two convergent curvilinear members.

Clause 5: The structural unit according to any of the preceding Clauses, wherein each meander member of the plurality of meander members is connected to an adjacent meander member of the plurality of meander members.

Clause 6: The structural unit according to any of the preceding Clauses further comprising a plurality of electrodes attached to the structural unit.

Clause 7: The structural unit according to Clause 6, wherein the plurality of electrodes comprises a first electrode disposed between the proximal member and the plurality of divergent curvilinear members.

Clause 8: The structural unit according to Clauses 6 or 7, wherein the plurality of electrodes comprises one or more electrodes disposed between adjacent meander members of the plurality of meander members.

Clause 9: The structural unit according to Clauses 6-8, wherein each electrode of the plurality of electrodes is formed by vacuum deposition directly onto the structural unit.

Clause 10: The structural unit according to Clause 9, the vacuum deposition comprising physical vapor deposition.

Clause 11: The structural unit according to Clause 9, the vacuum deposition comprising chemical vapor deposition.

Clause 12: The structural unit according to any of Clauses 6-11, further comprising a reference electrode attached to the structural unit.

Clause 13: The structural unit according to Clause 12, wherein the reference electrode is positioned proximate an electrode of the plurality of electrodes.

Clause 14: The structural unit according to any of the preceding Clauses, the structural unit being configured to transition between a collapsed configuration and an expanded configuration.

Clause 15: The structural unit according to any of the preceding Clauses, wherein the structural unit is formed from a planar sheet of resilient material.

Clause 16: The structural unit according to Clause 15, wherein the planar sheet of material comprises nitinol.

Clause 17: An end effector for a medical probe comprising: a plurality of structural members connected to each other and forming a generally cylindrical structure, each structural member of the plurality of structural members comprising: a proximal member extending along a longitudinal axis, the proximal member defining a plurality of divergent curvilinear members; each divergent curvilinear member defining two meander members extending along the longitudinal axis such that the structural member comprises a plurality of meander members, each of the plurality of meander members being connected to a respective convergent curvilinear member of a plurality of convergent curvilinear members; and a distal member connected to the plurality of convergent curvilinear members.

Clause 18: The end effector of Clause 17, wherein the end effector is configured to transition between a collapsed configuration and an expanded configuration.

Clause 19: The end effector according to Clauses 17 or 18, wherein each meander member of the plurality of meander members is connected to an adjacent meander member of the plurality of meander members.

Clause 20: The end effector according to any of Clauses 17-19 further comprising a plurality of electrodes attached to the generally cylindrical structure.

Clause 21: The end effector according to Clause 20, wherein the plurality of electrodes comprises a first electrode disposed between the proximal member and the plurality of divergent curvilinear members.

Clause 22: The end effector according to Clauses 20 or 21, wherein the plurality of electrodes comprises one or more electrodes disposed between adjacent meander members of the plurality of meander members.

Clause 23: The end effector according to any of Clauses 20-22, wherein each electrode of the plurality of electrodes is formed by vacuum deposition directly onto the generally cylindrical structure.

Clause 24: The end effector according to Clause 23, the vacuum deposition comprising physical vapor deposition.

Clause 25: The end effector according to Clause 23, the vacuum deposition comprising chemical vapor deposition.

Clause 26: The end effector according to any of Clauses 20-25, further comprising a reference electrode attached to the generally cylindrical structure.

Clause 27: The end effector according to Clause 26, wherein the reference electrode is positioned proximate an electrode of the plurality of electrodes.

Clause 28: The end effector according to any of the preceding Clauses, wherein the structural unit is formed from a planar sheet of resilient material.

Clause 29: The end effector according to Clause 28, wherein the planar sheet of material comprises nitinol.

Clause 30: The end effector according to any of Clauses 20-29, further comprising one or more electrical traces formed on each structural member, each electrical trace being connected to a respective electrode of the plurality of electrodes.

Clause 31: The end effector according to Clause 30, further comprising a plurality of reference electrodes, each reference electrode of the plurality of reference electrodes being positioned proximate a respective electrode of the plurality of electrodes and attached to a respective structural member of the plurality of structural members on a side of the respective structural member opposite each respective electrode of the plurality of electrodes.

Clause 32: The end effector according to any of Clauses 17-31, further comprising an electromagnetic coil attached to the cylindrical structure, the electromagnetic coil configured to detect a magnetic field for position sensing.

Clause 33: The end effector according to any one of Clauses 17-32, the plurality of structural members being connected to a distal hub at a distal end of the generally cylindrical structure.

Clause 34: The end effector according to Clause 33, wherein the distal hub is positioned proximal to the distal end of the generally cylindrical structure.

Clause 35: A structural unit for an end effector comprising: a proximal member extending along a longitudinal axis; a first divergent curvilinear member connected to a distal end of the proximal member; a second divergent curvilinear member connected to the distal end of the proximal member; a first meander member connected to a distal end of the first divergent curvilinear member; a second meander member connected to the distal end of the first divergent curvilinear member; a third meander member connected to a distal end of the second divergent curvilinear member; a fourth meander member connected to the distal end of the second divergent curvilinear member; a first convergent curvilinear member, the first meander member and the second meander member being connected to the first convergent curvilinear member; a second convergent curvilinear member, the third meander member and the fourth meander member being connected to the second convergent curvilinear member; and a distal member connected to the first convergent curvilinear member and the second convergent curvilinear member.

Clause 36: The structural unit of Clause 35, wherein the first meander member is further connected to the second meander member.

Clause 37: The structural unit of Clauses 35 or 36, wherein the second meander member is further connected to the first meander member and the third meander member.

Clause 38: The structural unit of any of Clauses 35-37, wherein the third meander member is further connected to the second meander member and the fourth meander member.

Clause 39: The structural unit of any of Clauses 35-38, wherein the fourth meander member is further connected to the third meander member.

Clause 40: The structural unit of any of Clauses 35-39 further comprising an electrode connected to the structural unit.

Clause 41: The structural unit of Clause 40, wherein the electrode is positioned between the proximal member, the first divergent curvilinear member, and the second divergent curvilinear member.

Clause 42: The structural unit of Clause 40, wherein the electrode is positioned between the first divergent curvilinear member, the first meander member, and the second meander member.

Clause 43: The structural unit of Clause 40, wherein the electrode is positioned between the second divergent curvilinear member, the third meander member, and the fourth meander member.

Clause 44: The structural unit of Clause 40, wherein the electrode is positioned between the first meander member and the second meander member.

Clause 45: The structural unit of Clause 40, wherein the electrode is positioned between the first meander member, the second meander member, and the first convergent curvilinear member.

Clause 46: The structural unit of Clause 40, wherein the electrode is positioned between the third meander member, the fourth meander member, and the second convergent curvilinear member.

Clause 47: The structural unit of Clause 40, wherein the electrode is positioned between the first convergent curvilinear member, the second convergent curvilinear member, and the distal member.

Clause 48: A method of constructing a medical probe, the method comprising: forming a plurality of spines from a planar sheet of material; forming a plurality of electrodes on the planar sheet of material by vacuum deposition; forming a plurality of electrical traces on the planar sheet of material, each electrical trace of the plurality of electrical traces being connected to a respective electrode of the plurality of electrodes; and connecting opposite ends of the planar sheet of material to each other to form a cylindrical structure.

Clause 49: The method according to Clause 48, wherein the planar sheet of material comprises nitinol.

Clause 50: The method according to Clauses 48 or 49, the cylindrical structure being configured to transition between a collapsed configuration and an expanded configuration.

Clause 51: The medical probe according to any of Clauses 48-50, the cylindrical structure comprising a substantially planar distal portion.

Clause 52: The method according to any of Clauses 48-51, the vacuum deposition comprising physical vapor deposition.

Clause 53: The method according to any of Clauses 48-51, the vacuum deposition comprising chemical vapor deposition.

Clause 54: The method according to any of Clauses 48-53, each spine of the plurality of spines comprising a curvilinear spine.

Clause 55: The method according to any of Clauses 48-54, wherein each electrode is positioned at an intersection between two adjacent spines of the plurality of spines.

Clause 56: The method according to any of Clauses 48-55, further comprising attaching a reference electrode to the cylindrical structure.

Clause 57: The method according to Clause 56, further comprising positioning the reference electrode proximate an electrode of the plurality of electrodes.

Clause 58: The method according to Clause 57, further comprising attaching a plurality of reference electrodes to the cylindrical structure, each reference electrode of the plurality of reference electrodes being positioned proximate a respective electrode of the plurality of electrodes and attached to a respective spine of the plurality of spines on a side of the respective spine opposite each respective electrode of the plurality of electrodes.

Clause 59: The method according to any of Clauses 48-58 further comprising attaching an electromagnetic coil to the cylindrical structure, the electromagnetic coil configured to detect a magnetic field for position sensing.

15
16

Clause 60: The method according to any one of Clauses 48-59, the plurality of spines converging to a distal hub at a distal end of the cylindrical structure.

Clause 61: The method according to Clause 60, wherein the distal hub is positioned proximal to the distal end of the cylindrical structure.

Clause 62: The method according to any of Clauses 48-61, wherein at least one of the plurality of electrodes is configured for mapping electrical signals in a heart of a patient.

Clause 63: The method according to any of Clauses 48-62, wherein at least one electrode of the plurality of electrodes is configured for ablating tissue in a heart of a patient.

Clause 64: The method according to Clause 63, wherein the at least one electrode is positioned at a distal end of the cylindrical structure.

Clause 65: The method according to Clause 63, wherein the one or more electrodes of the plurality of electrodes are configured to deliver electrical pulses for irreversible electroporation, the pulses having a peak voltage of at least 900 volts (V).

The embodiments described above are cited by way of example, and the present invention is not limited by what has been particularly shown and described hereinabove. Rather, the scope of the invention includes both combinations and sub combinations of the various features described hereinabove, as well as variations and modifications thereof which would occur to persons skilled in the art upon reading the foregoing description and which are not disclosed in the prior art.

What is claimed is:

1. A structural unit for an end effector comprising:
   a proximal member extending along a longitudinal axis, the proximal member defining a plurality of divergent curvilinear members;
   each divergent curvilinear member defining two meander members extending along the longitudinal axis such that the structural unit comprises a plurality of meander members, each of the plurality of meander members being connected to a respective convergent curvilinear member of a plurality of convergent curvilinear members; and
   a distal member connected to the plurality of convergent curvilinear members, the structural unit being configured to transition between a collapsed configuration and an expanded configuration, the expanded configuration forming a generally cylindrical structure comprising:
      a circumferential surface portion extending around the longitudinal axis; and
      a substantially planar distal portion perpendicular to the longitudinal axis.

2. The structural unit according to claim 1, wherein each meander member of the plurality of meander members is connected to an adjacent meander member of the plurality of meander members.

3. The structural unit according to claim 1, further comprising a plurality of electrodes attached to the structural unit.

4. The structural unit according to claim 3, wherein the plurality of electrodes comprises one or more electrodes disposed between adjacent meander members of the plurality of meander members.

5. The structural unit according to claim 1, the generally cylindrical structure comprising a rounded transition portion connecting the circumferential surface portion to the planar distal portion.

6. An end effector for a medical probe comprising:
   a plurality of structural members connected to each other and forming a generally cylindrical structure, the generally cylindrical structure comprising a circumferential surface portion extending around a longitudinal axis and a substantially planar distal portion perpendicular to the longitudinal axis, each structural member of the plurality of structural members comprising:
      a proximal member extending along a longitudinal axis, the proximal member defining a plurality of divergent curvilinear members;
      each divergent curvilinear member defining two meander members extending along the longitudinal axis such that the structural member comprises a plurality of meander members, each of the plurality of meander members being connected to a respective convergent curvilinear member of a plurality of convergent curvilinear members; and
      a distal member connected to the plurality of convergent curvilinear members.

7. The end effector of claim 6, wherein the end effector is configured to transition between a collapsed configuration and an expanded configuration.

8. The end effector according to claim 6, wherein each meander member of the plurality of meander members is connected to an adjacent meander member of the plurality of meander members.

9. The end effector according to claim 6, further comprising a plurality of electrodes attached to the generally cylindrical structure.

10. The end effector according to claim 9, wherein the plurality of electrodes comprises a first electrode disposed between the proximal member and the plurality of divergent curvilinear members.

11. The end effector according to claim 9, wherein each electrode of the plurality of electrodes is formed by vacuum deposition directly onto the generally cylindrical structure.

12. The end effector according to claim 9, further comprising a reference electrode attached to the generally cylindrical structure.

13. The end effector according to claim 12, wherein the reference electrode is positioned proximate an electrode of the plurality of electrodes.

14. The end effector according to claim 9, further comprising one or more electrical traces formed on each structural member, each electrical trace being connected to a respective electrode of the plurality of electrodes.

15. The end effector according to claim 6, further comprising an electromagnetic coil attached to the generally cylindrical structure, the electromagnetic coil configured to detect a magnetic field for position sensing.

16. A method of constructing a medical probe, the method comprising:
   forming a plurality of spines from a planar sheet of material;
   forming a plurality of electrodes on the planar sheet of material by vacuum deposition;
   forming a plurality of electrical traces on the planar sheet of material, each electrical trace of the plurality of electrical traces being connected to a respective electrode of the plurality of electrodes; and
   connecting opposite ends of the planar sheet of material to each other to form a cylindrical structure comprising a circumferential surface portion extending around a longitudinal axis and a substantially planar distal portion perpendicular to the longitudinal axis.

17. The method according to claim 16, the cylindrical structure being configured to transition between a collapsed configuration and an expanded configuration.

18. The method according to claim 16, each spine of the plurality of spines comprising a curvilinear spine.

19. The method according to claim 16, wherein each electrode is positioned at an intersection between two adjacent spines of the plurality of spines.

20. The method according to claim 19, further comprising attaching a plurality of reference electrodes to the cylindrical structure, each reference electrode of the plurality of reference electrodes being positioned proximate a respective electrode of the plurality of electrodes and attached to a respective spine of the plurality of spines on a side of the respective spine opposite each respective electrode of the plurality of electrodes.

\* \* \* \* \*